(12) United States Patent
Doyle

(10) Patent No.: US 9,724,161 B2
(45) Date of Patent: Aug. 8, 2017

(54) SYSTEMS, APPARATUSES AND METHODS OF TOOL EXCHANGE

(75) Inventor: Mark Doyle, Del mar, CA (US)

(73) Assignee: CAREFUSION 2200, INC., San Diego, CA (US)

( * ) Notice: Subject to any disclaimer, the term of this patent is extended or adjusted under 35 U.S.C. 154(b) by 1269 days.

(21) Appl. No.: 13/704,174

(22) PCT Filed: Jun. 16, 2011

(86) PCT No.: PCT/US2011/040627
§ 371 (c)(1),
(2), (4) Date: Apr. 2, 2013

(87) PCT Pub. No.: WO2011/159860
PCT Pub. Date: Dec. 22, 2011

(65) Prior Publication Data
US 2013/0184690 A1 Jul. 18, 2013

Related U.S. Application Data

(60) Provisional application No. 61/355,938, filed on Jun. 17, 2010.

(51) Int. Cl.
| | |
|---|---|
| *B25B 5/00* | (2006.01) |
| *A61B 19/00* | (2006.01) |
| *A61B 34/00* | (2016.01) |
| *A61B 17/00* | (2006.01) |
| *A61B 17/29* | (2006.01) |

(52) U.S. Cl.
CPC .............. *A61B 19/22* (2013.01); *A61B 34/70* (2016.02); *A61B 2017/0046* (2013.01); *A61B 2017/00362* (2013.01); *A61B 2017/00464* (2013.01); *A61B 2017/00473* (2013.01); *A61B 2017/2931* (2013.01)

(58) Field of Classification Search
CPC ....... B25B 1/14; B25B 1/2321; B25B 1/2484; B25B 5/04; B25B 1/00
See application file for complete search history.

(56) References Cited

U.S. PATENT DOCUMENTS

| | | |
|---|---|---|
| 5,464,300 A | 11/1995 | Crainich |
| 5,865,361 A | 2/1999 | Milliman et al. |
| 5,893,875 A | 4/1999 | O'Connor et al. |

(Continued)

OTHER PUBLICATIONS

Extended European Search Report of related European Patent Application No. 11796410.6 dated Mar. 24, 2017.

*Primary Examiner* — Lee D Wilson
(74) *Attorney, Agent, or Firm* — Arent Fox LLP

(57) ABSTRACT

A system for exchanging at least one end tool includes at least one tool exchange device for retaining each of the at least one end tool and at least one operating instrument engageable with each of the at least one end tool. The tool exchange device includes a tool retaining mechanism having an opening and a plurality of engagement features to enable mutually exclusive engagement and disengagement of the tool retaining mechanism with each of the at least one tool. Each of the at least one tool is receivable in the opening and has a biasing member engageable with the plurality of engagement features for at least one of biasing to an engaged position and a disengaged position.

38 Claims, 33 Drawing Sheets

(56) References Cited

U.S. PATENT DOCUMENTS

| | | | |
|---|---|---|---|
| 6,902,160 B1* | 6/2005 | Zajac, Jr. | B25B 5/16 269/24 |
| 8,132,801 B2* | 3/2012 | Miyashita | B25B 5/087 269/228 |
| 8,256,755 B2* | 9/2012 | Hiromatsu | B25B 5/087 269/228 |
| 2002/0111604 A1 | 8/2002 | Doyle et al. | |
| 2002/0143319 A1 | 10/2002 | Brock | |
| 2005/0283137 A1 | 12/2005 | Doyle et al. | |
| 2008/0179375 A1 | 7/2008 | Scirica | |
| 2013/0184690 A1* | 7/2013 | Doyle | A61B 19/22 606/1 |

* cited by examiner

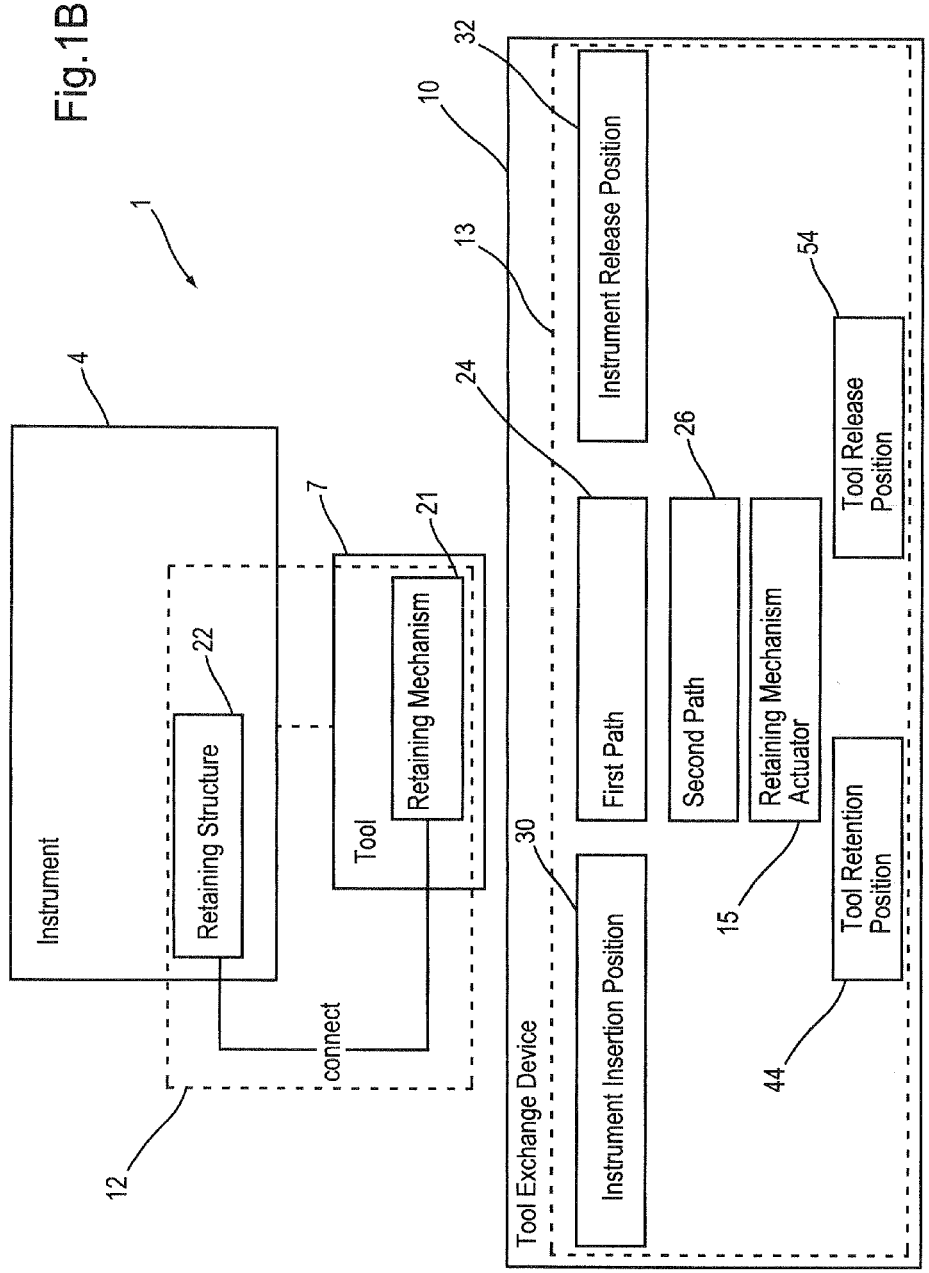

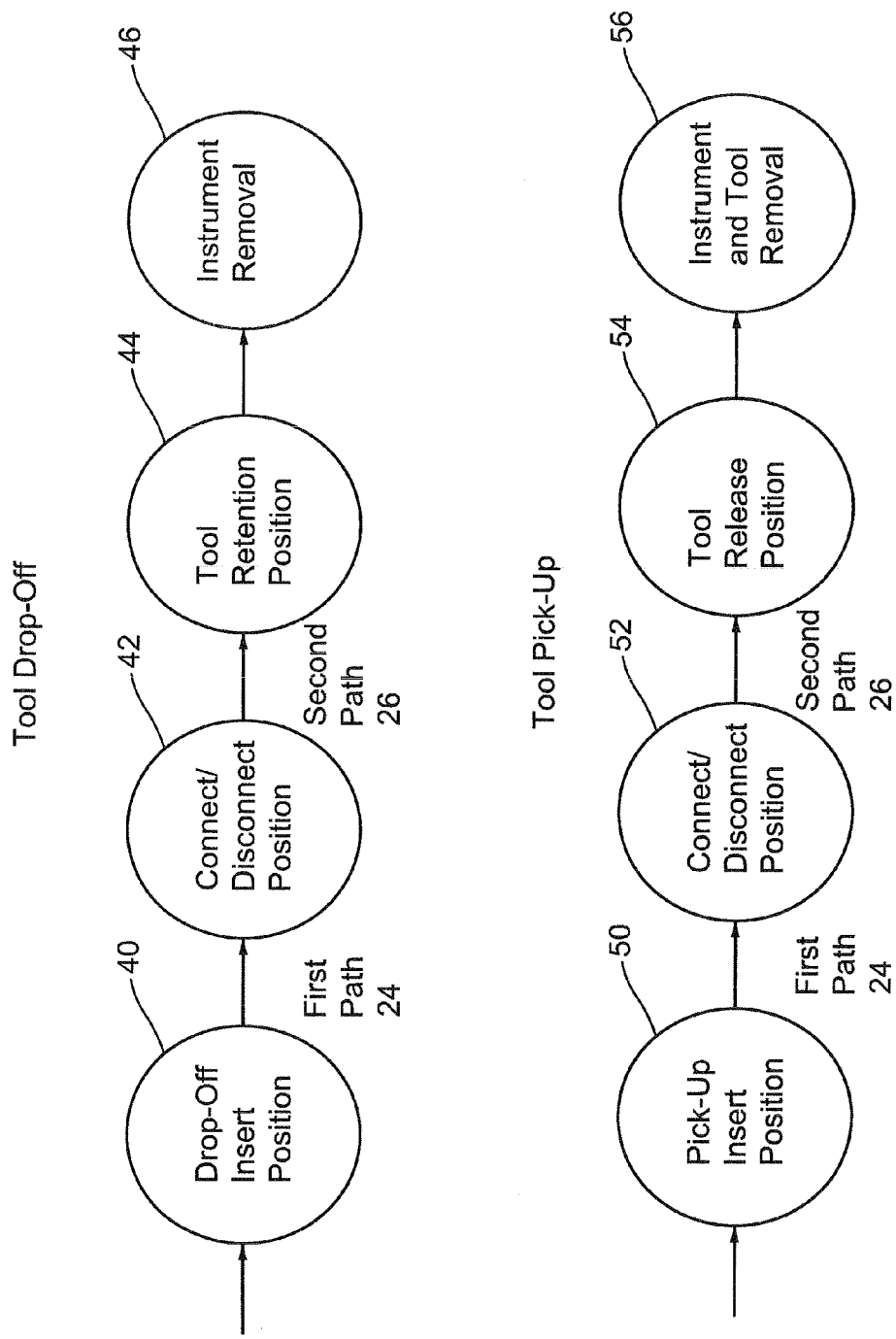

SYSTEMS, APPARATUSES AND METHODS OF TOOL EXCHANGE

CROSS-REFERENCE TO RELATED APPLICATION

This application is a National Stage entry of International Application No. PCT/US2011/040627 filed Jun. 16, 2011, which claims priority to U.S. Provisional Patent Appl. No. 61/355,938 filed Jun. 17, 2010, the disclosure of the prior applications are hereby incorporated in their entirety by reference.

This application claims priority to Applicant's co-pending U.S. Provisional Patent Application No. 61/355,938 titled "APPARATUS AND METHODS OF TOOL EXCHANGE" filed Jun. 17, 2010. This application is also related to Applicant's co-pending PCT Patent Appl. No. PCT/US11/22086 titled "HYDRAULIC DEVICE INCLUDING A SPOOL VALVE" filed Jan. 21, 2011, claiming priority to U.S. Patent Appl. No. 61/297,630 titled "HYDRAULIC DEVICE INCLUDING A SPOOL VALVE" filed on Jan. 22, 2010; and is related to PCT Patent Appl. No. PCT/US11/22562 titled "OVERFORCE MECHANISM" filed Jan. 26, 2011, claiming priority to U.S. Provisional Patent Appl. No. 61/298,784 titled "OVERFORCE MECHANISM" filed on Jan. 27, 2010; and is related to PCT Patent Appl. No. PCT/US10/46619 titled "ARTICULATED SURGICAL TOOL," filed Aug. 25, 2010, claiming priority to U.S. Provisional Patent Appl. No. 61/237,042 titled "ARTICULATED SURGICAL TOOL" filed on Aug. 26, 2009. The entirety of each of the foregoing is hereby incorporated by reference herein.

BACKGROUND

Field of the Invention

Aspects of the present invention relate to instruments, and more particularly, to apparatus and methods of tool exchange.

Background

Many related art technologies utilize instruments or tools to perform various functions. It is often desired to utilize a single apparatus to operate many different instruments or tools. As such, related art systems for holding and exchanging various instruments or tools have been developed.

For example, in a surgical application in the related art, in order for a surgeon to perform a surgical procedure, current tools require the repeated entry and exit of the tool into and out of the body during the surgery when the tool needs to be changed to perform a different action. Among other things, this approach may introduce additional risk to the patient, due to increased risk of infection due to the repeated entry into the patient's body. Also, the risk that one of the numerous tools that may be used during a surgery can be left inside the body of the patient after the conclusion of the surgery is magnified when multiple tools are brought into and taken out of the body of the patient during the procedure. In addition, such related art approaches may result in significant loss of time and/or resources during or when preparing for surgery, as well as in other contexts.

Thus, whether in a surgical application or in any other application, improvements in tool exchange are desired.

SUMMARY

While discussion of the aspects of the present invention that follows uses surgery for an illustrative purpose, it should be appreciated that the environment hereof is not limited to surgery and may include a variety of other environments. For example, aspects of the present invention may be used in manufacturing, construction, assembly lines, handling and disposing of hazardous materials, underwater manipulations, handling high temperature materials, or any other suitable environment where a user may be remote from the item being manipulated or may experience fatigue when operating a mechanical device.

An aspect of the present invention is directed to a system for exchanging at least one end tool. The system includes at least one tool exchange device for retaining each of the at least one end tool and at least one operating instrument engageable with each of the at least one end tool. The tool exchange device includes a tool retaining mechanism having an opening and a plurality of engagement features to enable mutually exclusive engagement and disengagement of the tool retaining mechanism with each of the at least one tool. Each of the at least one tool is receivable in the opening and has a biasing member engageable with the plurality of engagement features for at least one of biasing to an engaged position and a disengaged position.

An aspect of the present invention is directed to a method for exchanging a plurality of tools. The method includes inserting an operating instrument engaged with an end tool into a tool exchange device having a biasing member along a first direction. The method further includes engaging the biasing member with a plurality of engagement features of the tool exchange device, thereby releasing the engagement of the operating instrument with the tool. The method also comprises moving the operating instrument and tool along a second direction contemporaneously with maintaining engagement with the plurality of engagement features, thereby releasing the operating instrument from the end tool.

Another aspect of the present invention is directed to a system for exchanging at least one end tool comprising. The system includes at least one tool exchange device for retaining each of the at least one end tool and at least one operating instrument engageable with each of the at least one end tool. The tool exchange device includes a tool retaining mechanism having an opening and means for enabling mutually exclusive engagement and disengagement of the tool retaining mechanism with each of the at least one tool. Each of the at least one tool is receivable in the opening and has means for at least one of engaging or disengaging the means for enabling mutually exclusive engagement and disengagement.

Another aspect of the instant invention is directed to a retaining mechanism engageable with a tool exchange device. The tool exchange device includes a tool exchange acceptor portion mateable with a portion of the tool exchange device and a biasing member operably engageable with a portion of an operating instrument. The biasing member is configured to disengage from the portion of the operating instrument in response to the acceptor portion being engaged with the portion of the tool exchange device.

Aspects of the present invention may incorporate methods, features, and operations as shown and described in U.S. Pat. No. 6,607,475 to Doyle, et al., the entirety of which is incorporated herein by reference. However, it should be noted that aspects of the present invention are not limited in application to devices shown in U.S. Pat. No. 6,607,475 or in related patents and applications. Some aspects of the present invention provide an apparatus for controlling the micro-movements and macro-movements of hydraulically actuated devices, including an articulated surgical tool. In variations of the present invention, such aspects may enhance the control and manipulation of the device.

Aspects of the present invention provide benefits and advantages that include the ability to prevent unwanted or uncontrolled motion of tools, instruments and tools during in situ tool, instrument or device exchange. Thus, tool exchange can be made safer and more accurate, particularly in sensitive operating environments.

Additional advantages and novel features relating to aspects of the present invention will be set forth in part in the description that follows, and in part will become more apparent to those skilled in the art upon examination of the following or upon learning by practice thereof.

BRIEF DESCRIPTION OF THE DRAWINGS

Aspects of the present invention will become fully understood from the detailed description given herein below and the accompanying drawings, which are given by way of illustration and example only and thus not limited with respect to aspects of the present invention, wherein:

FIG. 1B is a second representative diagram of an example system including a tool exchange device in accordance with aspects of the invention;

FIG. 2 shows representative diagrams of various example actions involved in the tool exchange device interacting with a tool, in accordance with aspects of the invention;

DETAILED DESCRIPTION

Aspects of the present invention will now be described more fully hereinafter with reference to the accompanying drawings, in which variations and aspects of the present invention are shown. Aspects of the present invention may, however, be realized in many different forms and should not be construed as limited to the variations set forth herein; rather, the variations are provided so that this disclosure will be thorough and complete in the illustrative implementations, and will fully convey the scope thereof to those skilled in the art.

Unless otherwise defined, all technical and scientific terms used herein have the same meaning as commonly understood by one of ordinary skill in the art to which aspects of the present invention belong. The methods and examples provided herein are illustrative only and not intended to be limiting.

Overview of an Example Tool Exchange Device

Figure 1A:
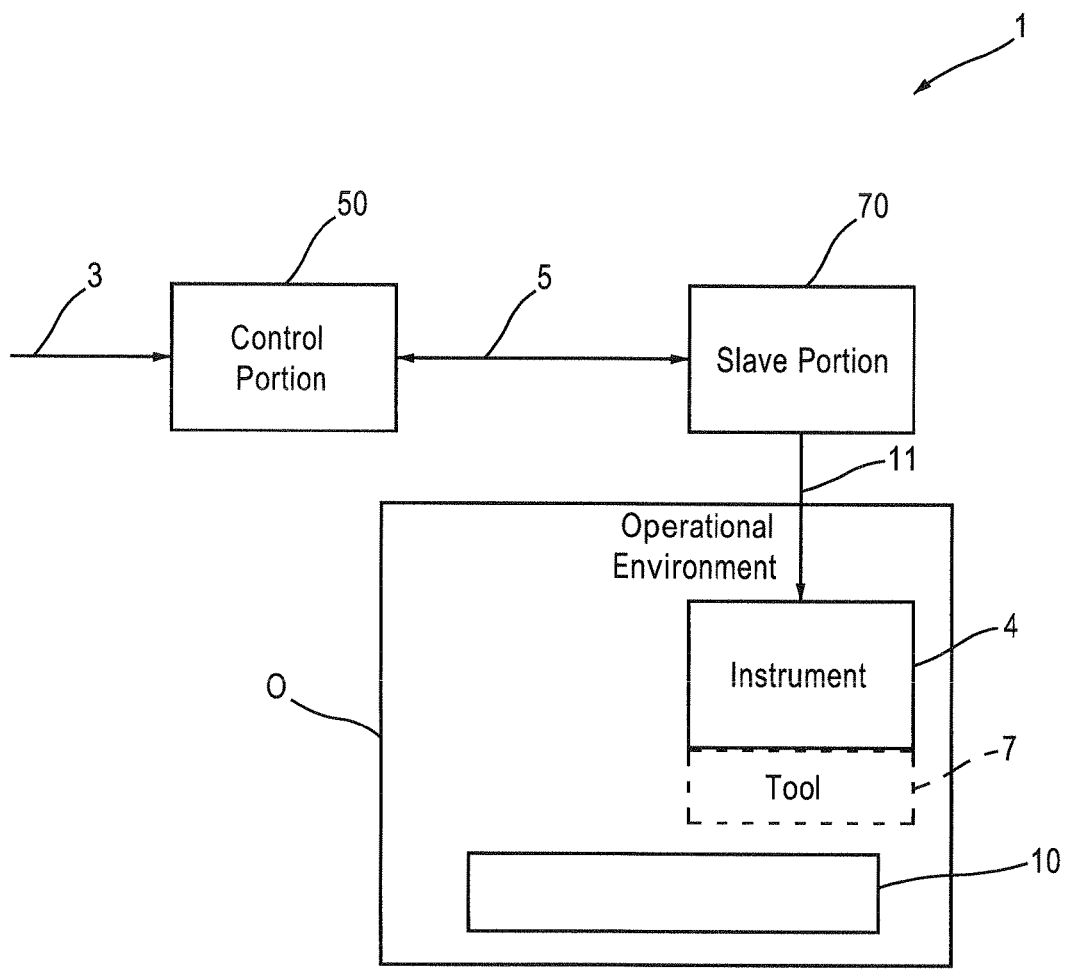
FIG. 1A is a first representative diagram of an example system including a tool exchange device in accordance with aspects of the invention.

FIGS. 1A and 1B show representative diagrams of example systems using a tool exchange, device in accordance with aspects of the invention.

As shown in FIG. 1A, the example holster or tool exchange device 10 may be used in an example device or system 1 for remotely controlling an articulating instrument 4 and/or tool 7 in a work environment O, for example, for performing surgery on a patient. Although the specific aspects of the device may vary according to the implementation, FIG. 1A shows a general overview of the relationship among system portions 1 and 10.

Instrument 4 may be used to insert or remove a tool 7, such as an end tool, as further referred to and described further herein (such tool 7 also interchangeably referred to herein as an "end tool"), with respect to a holster or tool exchange device 10 holding the end tool 7. In an aspect, the holster or tool exchange device 10 may be located in the vicinity of an ongoing surgical procedure, such as inside the body of a surgery patient. In the case where the end tool 7 is secured in the holster or tool exchange device 10, in order to remove the end tool 7 from the holster or tool exchange device 10, while securely retaining the end tool 7 on the instrument 4, the described aspects may provide a plurality of mechanisms and corresponding actions to avoid unintentional release of the end tool 7. In the case where the end tool 7 is secured on the instrument 4, in order to remove the end tool 7 from the instrument 4 while securely retaining the end tool 7 within the holster or tool exchange device 10, the described aspects may provide a plurality of mechanisms and corresponding actions, to avoid unintentional release of the end tool 7.

Although the example holster or tool exchange device 10 may be used with a variety of systems and in a variety of environments, it is described here in the context of a device 1 that includes a slave portion 70 remotely actuated by a control portion 50. The slave portion 70 includes at least one instrument 4 that can be connected to one or more different end tools 7, such as multifunctional or separate tools for performing various mechanical and/or other operations. In an aspect, the example holster or tool exchange device 10, among other things, allows the slave portion 70 of the device 1 to manipulate instrument 4 to securely attach and use, or securely detach and store, an end tool 7, for example in a surgical context, in situ, e.g., in the operating environment O. Further, although described herein with respect to a single end tool 7, it should be noted that holster or tool exchange device 10 may be configured to hold a plurality of end tools.

In an aspect, the device 1 may include a control portion 50 operable to receive an input 3, such as a force or motion, to drive the instrument 4 and/or end tool 7 connected to a slave portion 70 of the device. The input 3 is transferred from the control portion 50 to the slave portion 70 via a transfer mechanism 5, such as a hydraulic, electrically and/or electromagnetically driven system, or other system (e.g., otherwise controlled robotic system). Device 1 may be configured to provide a given correlation between input 3 and the resultant output 11 that operates instrument 4 and/or end tool 7 within an operational environment O. For example, input 3 may include a linear and/or rotational movement, and output 11 may be a linear and/or rotational movement, and such movements may be combined or correlated in any suitable fashion. For instance, a linear input 3 may be correlated to an output 11 that is linear or rotational, and a rotational input 3 may be correlated to an output 11 that is rotational or linear. Also, the relative degree of transfer may be controlled, e.g. such that a given amount of input 3 produces a given amount of output 11. Further, transfer mechanism 5 may additionally transfer feedback from instrument 4 and/or end tool 7 back to control portion 50, thereby providing a user with a direct, tactile feel for the work being performed by the instrument 4 and/or end tool 7. In one example of a suitable application for system or device 1, the instrument 4 and/or end tool 7 may include an articulating device for performing surgery within a portion of a body of a patient. Thus, device 1 provides a system to control, in a precise manner, actions of an instrument 4 and/or end tool 7 in an operational environment O from a remote location.

Further, in device 1, the control portion 50 may be capable of actuating both macro and micro movements, and the slave portion 70 may be capable of carrying out both macro and micro movements. Generally, these portions may be connected via transfer mechanism 5, such as hydraulic lines. The control portion can provide a user interface to allow actuation of aspects of the slave portion or portions via the hydraulic lines or other mechanisms. Although a particular configuration for the control and slave portions is shown in FIG. 1, it is to be understood that this is merely one example configuration. As will be shown, several alternative variations of the control and slave portions may also be used in conjunction with aspects of the invention.

FIG. 1B is a representative diagram of additional detailed features of a holster and/or tool exchange device 10 interacting with various portions of device 1 of the system of FIG. 1, in accordance with aspects of the invention. FIG. 1B shows the instrument 4 connected to the end tool 7, which in turn are connected to a holster or tool exchange device 10. As further shown in FIG. 1B, the holster or tool exchange device 10 may have several features cooperating to engage and/or disengage both the instrument 4 and the end tool 7.

In FIG. 1B, the end tool 7 and the instrument 4 may be connected as shown via complementary structures, such as a connection mechanism 21 on the end tool 7 and a connection structure 22 on the instrument 4. This connection may be actuated manually without recourse to another component, for example, or it may be actuated via another component, such as the connection/disconnection element 32 of the holster or tool exchange device 10. The connection mechanism 21 on the end tool 7 and a connection structure 22 may comprise part of a tool engaging system 12. In other variations, the connection mechanism 21 may be located on the instrument 4 and the connection structure 22 may be located on the end tool 7.

Overview of Tool/Instrument Connection Mechanism
Tool/Instrument System

It is noted that the tool/instrument system shown in FIG. 1A may be used with or without the holster or tool exchange device 10 as specifically shown and described with respect to FIG. 1B. In the example implementation of FIG. 1B, actuation of the connection structure 22 of the instrument 4 and the connection mechanism 21 of the end tool 7 may be performed manually, or by another method, but may otherwise proceed similarly to as described elsewhere herein.

The various general actions involved in carrying out instrument operation to drop-off and/or pick-up an end tool, which are further shown and described with respect to example devices herein, are shown in FIG. 2. For example, for end tool drop-off, as shown, an instrument with an attached end tool may be first brought to the holster at a drop-off insert position 40. The instrument and attached end tool may then be moved in a first path 24 (e.g., inserted in a first linear direction into a holster for an end tool), so as to reach a connect/disconnect position 42 of the end tool with respect to the holster. The instrument and attached end tool may then be moved along a second path (e.g., rotated in a first rotational direction), so that the end tool reaches a tool retention position 44. The instrument may then be removed 46 without the end tool, which is retained in the holster (e.g., by moving the instrument in the opposite direction along the first path 24).

For end tool pick-up, as shown in FIG. 2, the process may be essentially the reverse of the drop-off process. For example, the instrument without an attached end tool may be moved to pick-up insert position 50 and then moved to a connect/disconnect position 52 (e.g., by inserting the instrument into the holster along the first path 24). The instrument and engaged end tool may then be moved along the second path (e.g., rotated in a second rotational direction, opposite the first rotational direction) to a tool release position 54. The instrument and engaged end tool may then be removed from the holster 56 (e.g., by moving the instrument and attached end tool in the opposite linear direction from the insert direction along the first path 24).

If the end tool 7 and instrument 4 are to be used without a holster or tool exchange device 10 along the lines of FIG. 1B and as described with regard to FIG. 2, for example, additional safety precautions may be employed. Safety issues that may arise from the practice of using the end tool 7 and instrument 4 without such features as shown and described with respect to FIGS. 1B and 2 may include accidental dropping of an end tool 7 and/or failing to secure to the end tool 7 to the instrument 4, for example.

Various components and/or methods may be employed to connect the end tool 7 to the instrument 4, as shown in FIG. 1B, examples of which will now be described in greater detail.

Front-Actuated Dual Inter-Engaging System

FIGS. 3-16 show views and portions, some in cutaway, of various features of a tool exchange device in accordance with one example front-actuated dual inter-engaging system, in accordance with aspects of the present invention.

Figure 3:
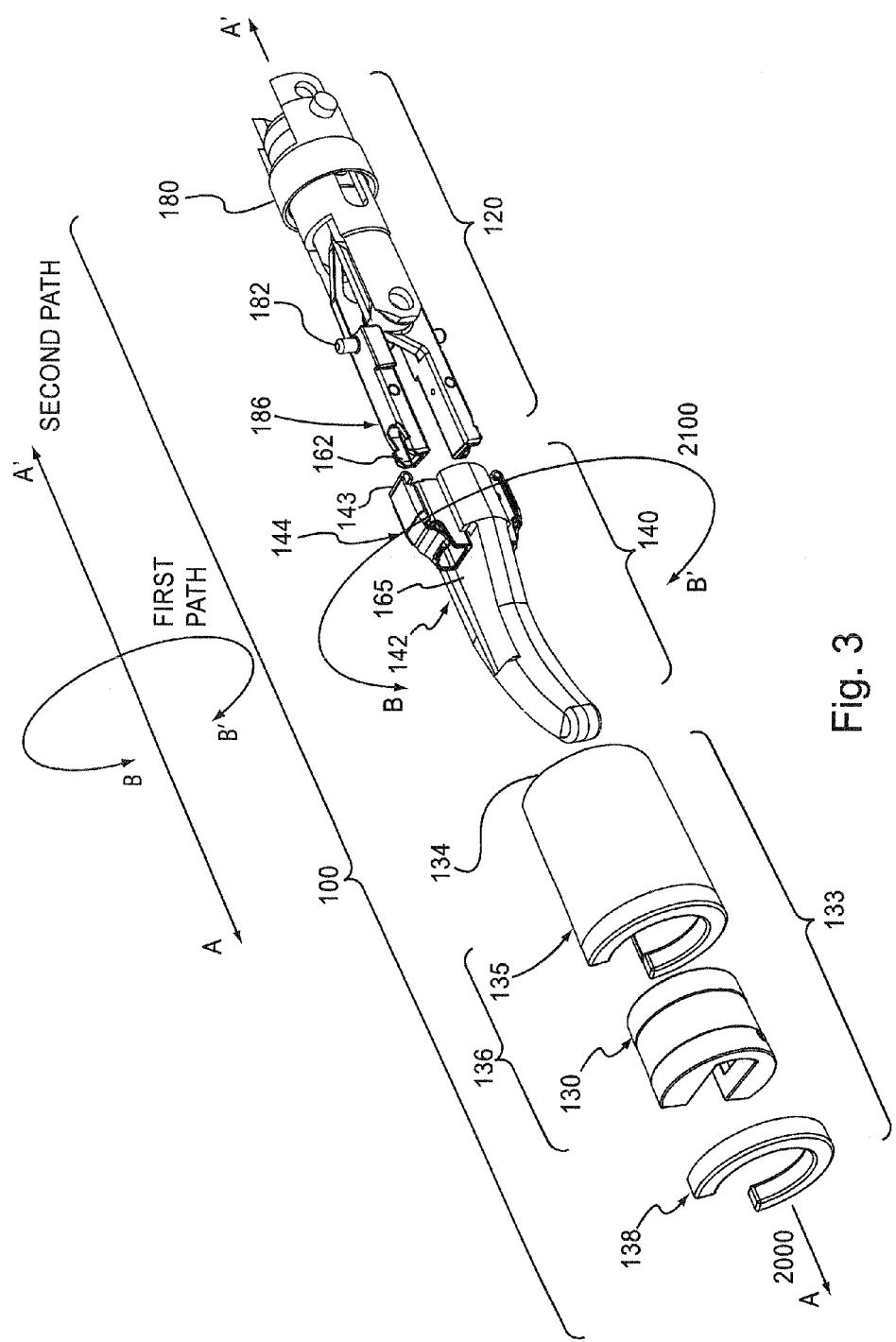
FIG. 3 is an exploded perspective view of an example of a front-actuated dual inter-engaging system, including a tool exchange device, in accordance with aspects of the current invention.
Figure 4:
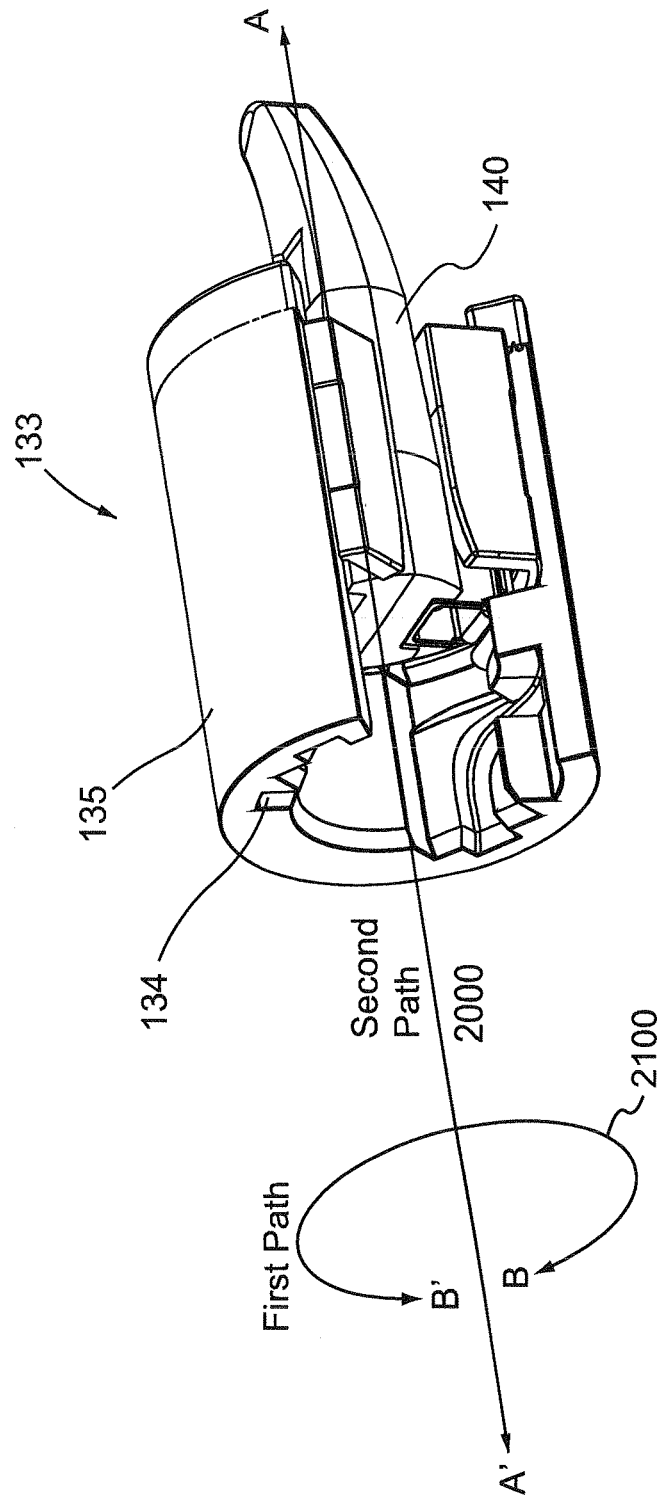
FIG. 4 is a perspective view of example first and second motions that may be used to engage and disengage engaging mechanisms on the tool exchange device of FIG. 3.
Figure 5:
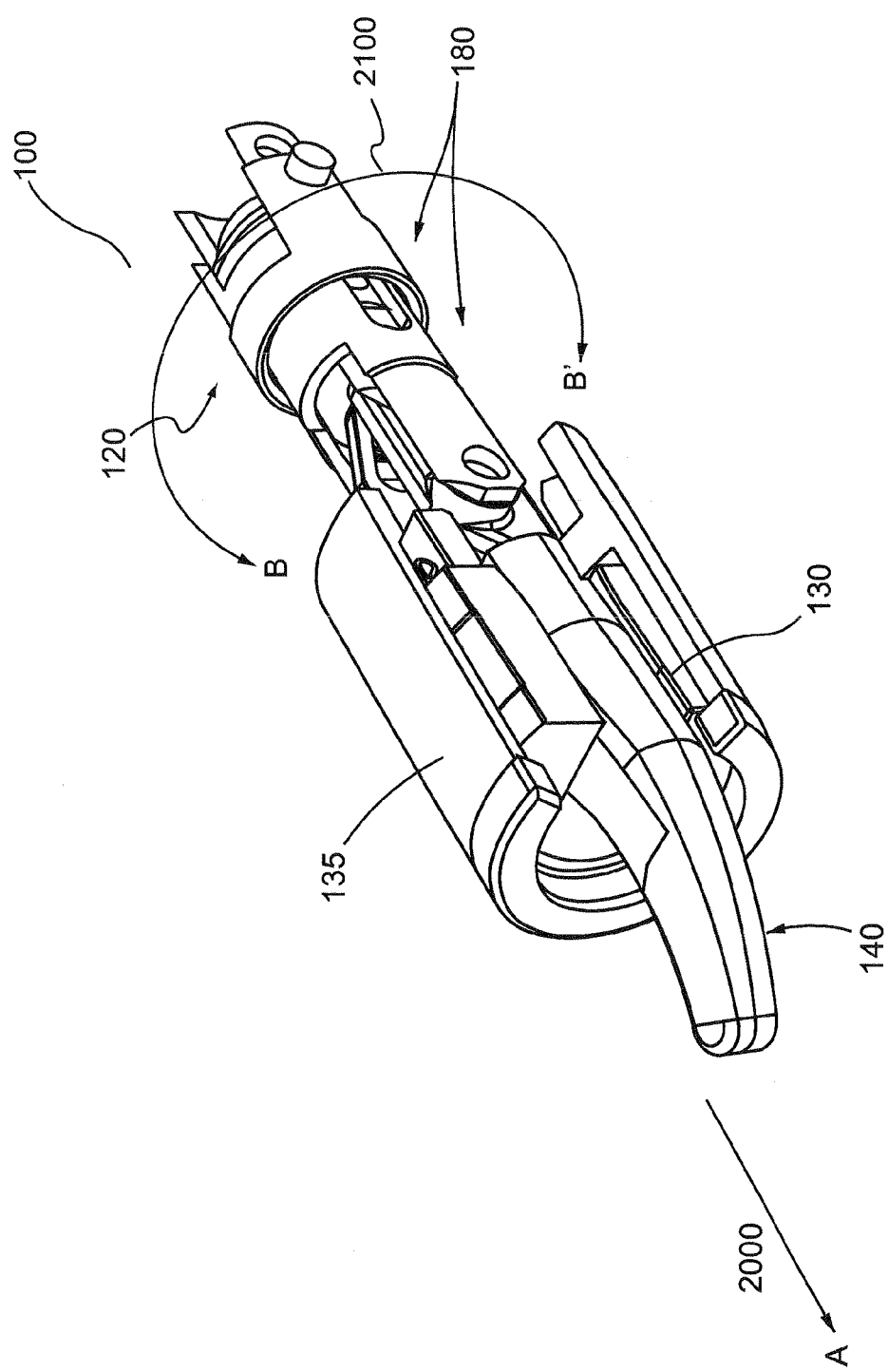
FIG. 5 shows perspective and partial sectional views of the system of FIG. 3, with the instrument in the tool exchange device and engaging the end tool.

FIG. 3 is an exploded perspective view of example portions of a front-actuated dual inter-engaging system, including a tool exchange device 133, in accordance with aspects of the current invention. FIG. 4 is a perspective partial cutaway view of example first and second motions that may be used to engage and disengage engaging mechanisms on the tool exchange device of FIG. 3. FIG. 5 shows a perspective partial sectional view of the system of FIG. 3, with the instrument in the tool exchange device and engaging the end tool.

Referring to FIGS. 3-5, according to example aspects of the current invention, a tool exchange system 100 includes an operating instrument 120 that is releasably connectable to an end tool 140. It should be understood that while a single tool exchange system 100 is discussed for clarity, it is within the scope of the overall system may include any number of tool exchange systems. For example, the overall system may allow for exchanging a plurality of tools by comprising a plurality of tool exchange systems, each corresponding to a distinct tool.

As shown in FIG. 4, the engaging and disengaging of the end tool 140 with the holster or tool exchange device 133 may be accomplished by moving the instrument to which the end tool 140 is attached sequentially along two motions, a first motion and a second motion. Note that each motion may be bi-directional and the two directions may be used to perform engaging and/or disengaging operations as described below.

In this example implementation, the first motion occurs along linear path 2000, and the second motion is in rotational path 2100, as shown in FIGS. 3-5. Moving the instrument 120 along the first and then the second motion will: 1) engage the end tool 140 with the holster 133 via a tool engaging system components 136, 2) engage an instrument via the holster 133 further via operating instrument engaging features operable with holster 133, 3) allow the end tool 140 to be disconnected from the instrument 120 and features operable with holster 133, and 4) disengage the instrument 120 from the holster 133. The instrument 120 may then be moved in the reverse (A') of the first motion direction (A) along path 2100 to 5) thereby allow the instrument 120 to be moved independently of the holster 133. Moving the instrument 120 again in the first (A) and then the second (A') motion will: 1) engage the instrument 120 with the holster 133, 2 allow the end tool 140 to be connected to the instrument 120, and, upon moving again in the first direction (opposite the original engagement direction, A') allow 3) the instrument 120 to disengage from the holster 133 with the engaged end tool 140 connected, and 4) allow the instrument 120 and end tool 140 to be used as a unit.

FIGS. 6-17 show views of various positions of the example system 100 of FIGS. 3-5. The instrument 120 may be engaged with the tool exchange system 100 so as to allow the instrument 120 to engage an end tool 140 and remove it from the holder 133, as follows. First, prior to engagement of the instrument 120 and end tool 140, the end tool 140 may be located inside the holster 133 (see FIG. 6). The instrument 186 is moved along the second path 2000 (e.g., in the direction A) so as to engage the tool exchange system containing the holster 133. The instrument 120 and the end tool 140 are then engaged with one another, as shown in FIG. 5. Subsequently, the instrument 120 and engaged end tool 140 may be rotated along a first direction B in rotational path 2100 (FIG. 5) to disengage the end tool 140 from the holster 133. The instrument 120 with the engaged end tool 140 may then be moved in direction A' to be used, for example, in one or more operative procedures.

Figure 6:
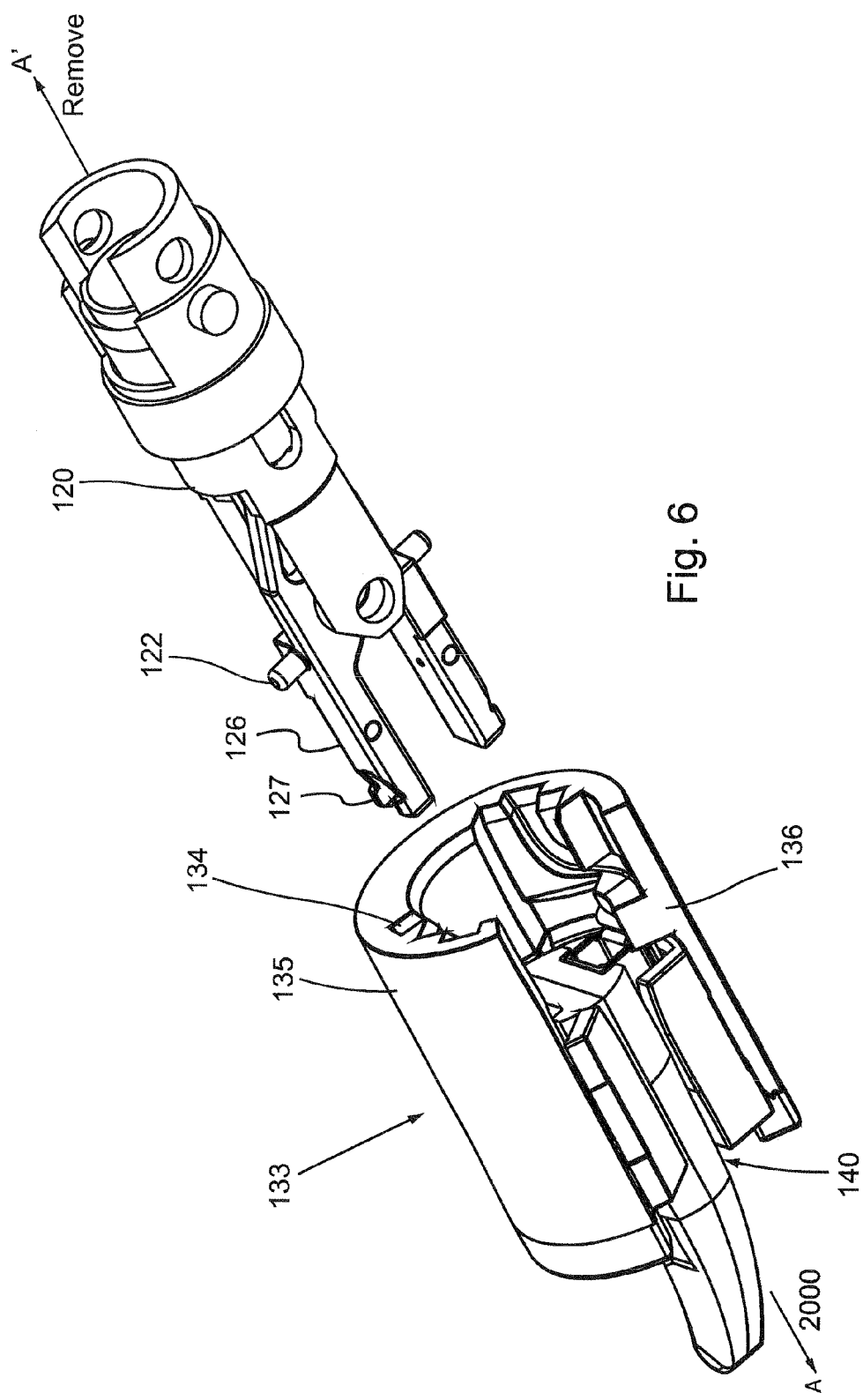
FIG. 6 is a perspective overview of the system of FIG. 3 upon disengaging the end tool and removing the instrument from the tool exchange device.

The operating instrument engaging system may thereafter be used to disengage the instrument 120 from the engaged end tool 140. The instrument 120 with the engaged end tool 140 (see FIG. 6) is used in direction A so as to engage the holster 133. The engaged instrument 120 and the end tool 140 may then be rotated in direction B' along rotational path 2100 (see FIG. 4) to a releasing position, 120 and the instrument 120 may then be disengaged from the end tool 140 (see, e.g., FIG. 6). At the releasing position 120, the instrument 120 is moved along a second direction A' in substantially the reverse direction as direction A along path 2000, as shown in FIG. 6. While the instrument 120 is moved along the second motion A', the end tool 140 is released from the instrument 120. Moving the instrument 120 along the second motion A' allows release by also disengaging various operating instrument engaging system portions, as described further with reference to FIGS. 8-17. The instrument 120 may thereby be removed from the tool exchange system. Since the holster 133 of the tool engaging system remains engaged with the end tool 140, the end tool 140 remains engaged inside the tool exchange system.

Figure 7:
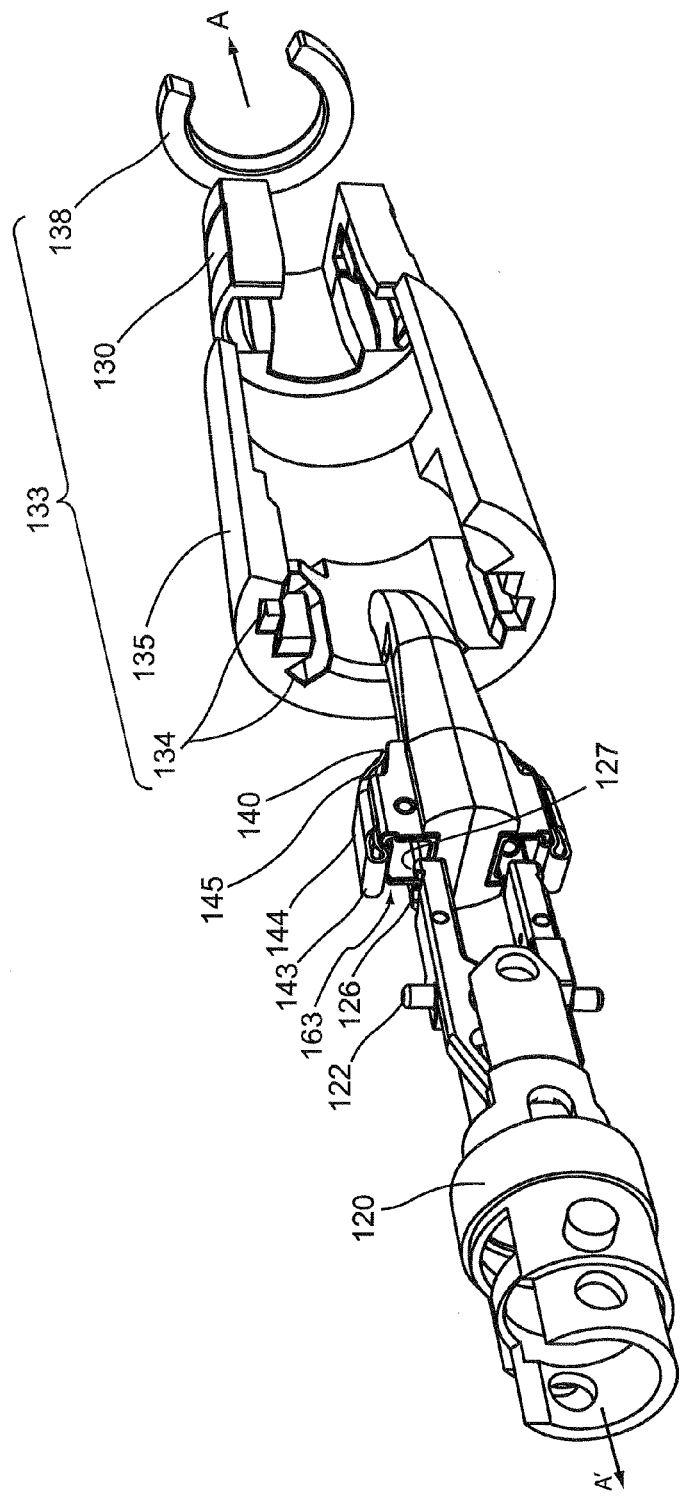
FIG. 7 illustrates a cross-sectional view of aspects of the instrument of FIG. 6 being removed from the housing.
Figure 8:
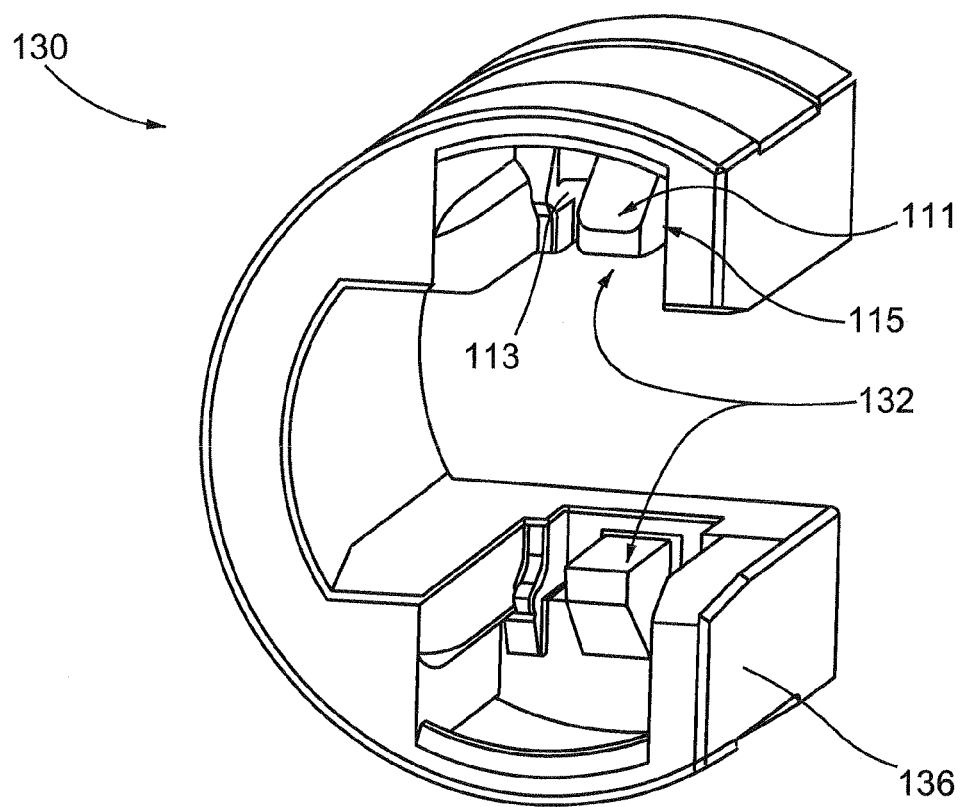
FIG. 8 is a perspective view of the barrel and the releasing structure in FIG. 3.
Figure 9:
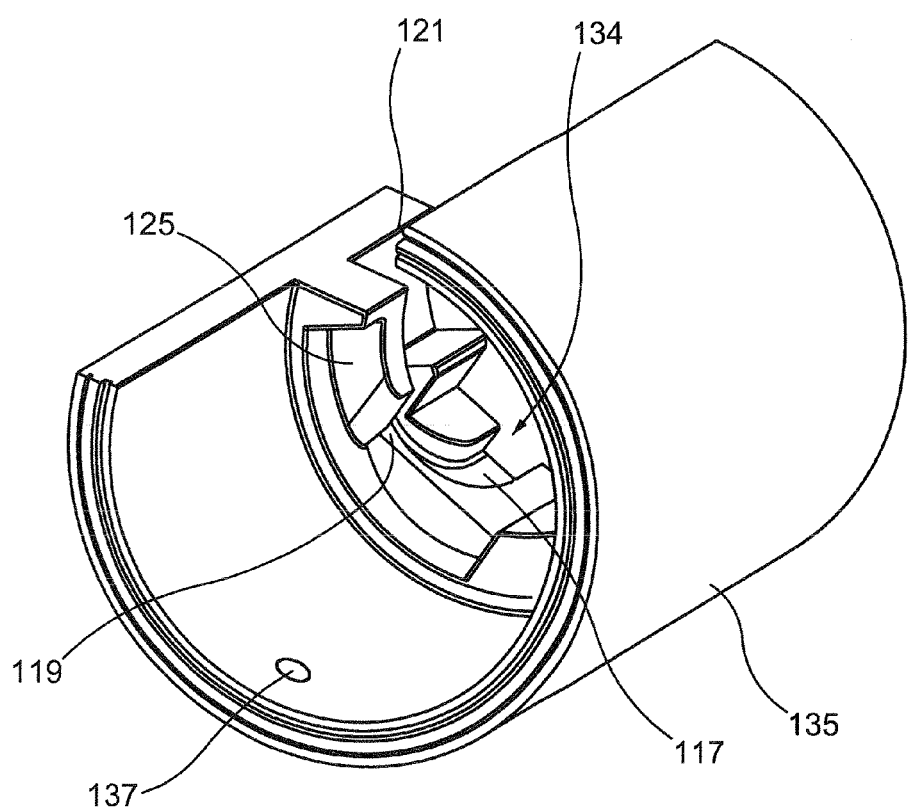
FIG. 9 is a perspective view of the tool accommodator in the front-actuated dual inter-engaging system of FIG. 3.
Figure 10:
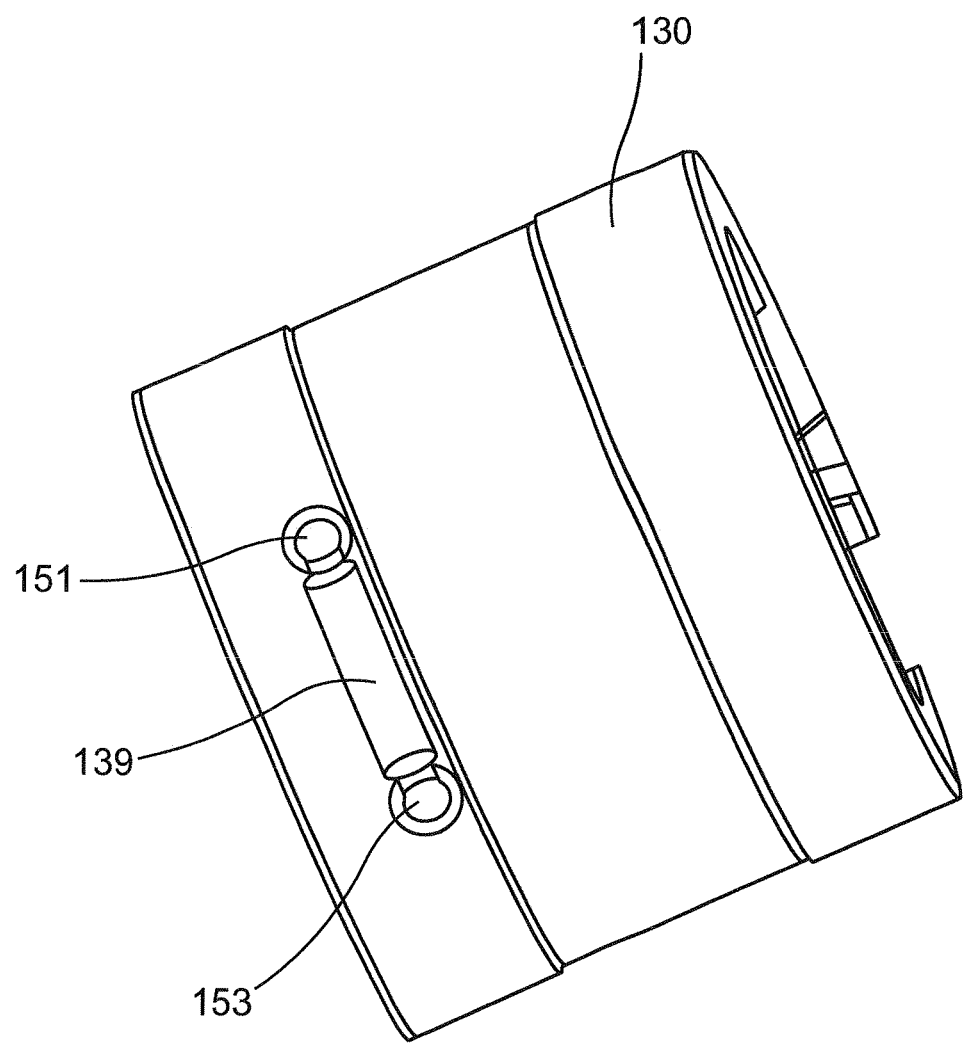
FIG. 10 is a perspective and partial sectional view of selected elements shown in FIG. 8.

FIGS. 8-10 show more detailed views of the engaging structure of the barrel of the example front-actuated dual inter-engaging system 100 of FIGS. 3-7. A connection element 132, as shown in FIG. 8, may be designed to cooperate with a securing structure 144 (also interchangeably referred herein as a biasing member) located on end tool 140 (see FIG. 11) and with a guiding structure 134 of a tool retaining mechanism 135, alternatively referred herein as a tool accommodator, as shown in FIG. 9, to releasably secure the end tool 140 relative to the barrel 130 within the tool accommodator 135. For example, in the example variation shown in FIG. 8, the connection element 132 includes a ramp having a first face 111 that radially moves a latch of an interacting end tool (see, e.g., latch 145 of end tool 140 shown in FIG. 11) upon axial movement of end tool 140 relative to barrel 130 (e.g., as shown and described with respect to FIGS. 3-7). Further, connection element 132 may include opposing side walls 113 and 115, for example, per FIG. 8, that oppose movement of latch 145 (FIG. 11) relative to barrel 130 to either secure end tool within barrel 130 or to allow the release of end tool after a secure connection of the end tool to and instrument, as further shown and describe with respect to FIGS. 3-7.

Figure 11:
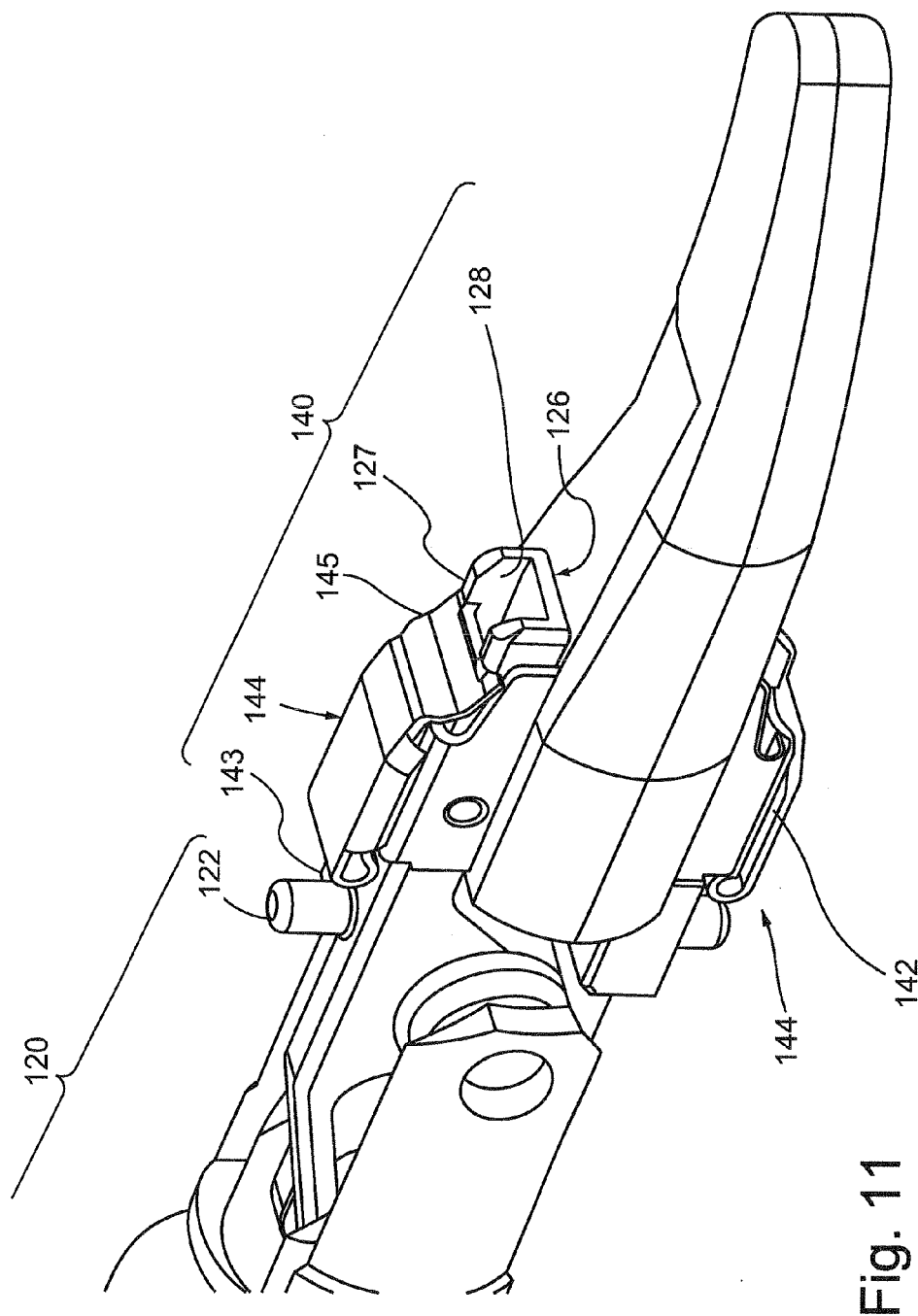
FIG. 11 is a perspective and partial cutaway view of the engaging of an end tool in the housing of the front-actuated dual inter-engaging system shown in FIG. 3.

Further, referring to FIGS. 8-10, barrel 130 and tool accommodator 135 may include cooperating rotational guide structures, such as a projection 137 on an inside wall of tool accommodator 135 and a recessed groove 139 on an outside wall of barrel 130, to direct relative rotational movement of the barrel 130 and tool accommodator 135. Furthermore, as shown in FIG. 10, recessed groove 139 may have one or more releasable engages, such as engages 151 and 153, to releasably position the barrel 130 relative to the tool accommodator 135 at one or more predetermined positions. In these aspects, for example, engages 151 and 153 may be usable to align portions of the guiding structure 134 in the tool accommodator 135 in order to position barrel 130 for insertion or removal of an end tool. Additionally, the guiding structure 134 may include various portions to direct relative movement for the secure attachment or release of the end tool relative to the barrel 130. In these aspects, for example, the guiding structure 134 may include a first portion 117 spaced apart from a second portion 121, both extending substantially parallel to a longitudinal axis of the tool accommodator 135, and radially interconnected by a third portion 119. As such, in this aspect, the guiding structure 134 forms a generally U-shaped channel within an internal wall of the tool accommodator, and movement of an instrument having an instrument guiding structure (see, e.g., instrument 120 having instrument guiding structure 122, as shown in FIG. 11), within guiding structure 134 may be cooperatively used to secure and/or release the end tool relative to the holster 133.

For example, in operation, the instrument 120 either inserts the end tool 140 in, or withdraws the end tool 140 from, the barrel 130 via axial and rotational movement relative to the holster 133, as shown and describe with respect to FIGS. 6-10. The holster 133 may be mounted to another securing structure that positions the holster 133 for access by the instrument 120. For example, according to a surgical aspects of the current invention, the holster 133 may be anchored inside a patient, such as within a holder mechanism in the patient, so that the instrument 120 may alternatively collect or deposit one or more selected end tool(s) 140 in respective holsters 133 without having to remove the instrument 120 and/or end tool 140 from within the body of the patient.

Figure 12:
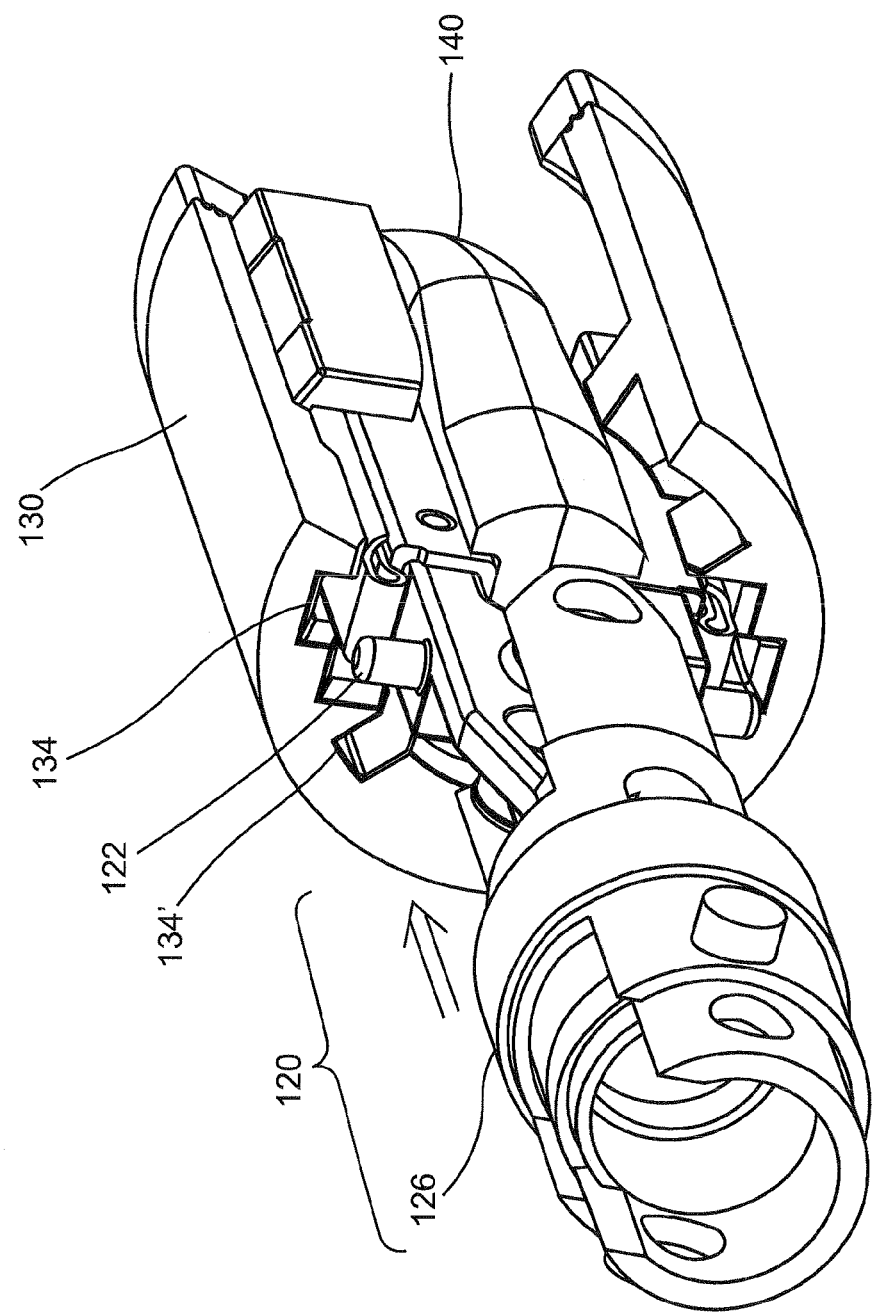
FIG. 12 illustrates aspects of the insertion of the instrument inside the housing of FIG. 10.

More specifically, the process of retrieving an end tool that is initially located with the tool exchange system will now be described in greater detail in conjunction with FIGS. 11-16. To engage the end tool 140 and the instrument 120, as shown in FIG. 12, for example, a first securing structure 126 of the instrument 120 may be placed inside an instrument receiving portion 163 of the end tool 140 and locked into place via second securing structure 144 (see, e.g., details of end tool 140 shown in FIG. 7). In one aspect, further shown in FIG. 11, the first securing structure 126 may include a tine having a raised end portion 127, and the second securing structure 144 may include a receiver 142, such as a tube sized to accept the tine, and a movable securing device, such as a latch 145 connected to a loop-shaped portion 143 that biases the latch 145 closed relative to the raised end portion 127 of the tine to securably engage or release the end tool 140 relative to the instrument 120.

As shown, for example, in FIG. 12, the holster 133 may also include an operating instrument engaging system that includes a tool accommodator portion 135 and a barrel portion 130. Example interaction between holster 133, the instrument 120 and the end tool 140 will now be discussed in greater detail.

When the instrument 120 is secured within the end tool 140, as described above, the instrument 120 and end tool 140 may be moved into the holster 133, as shown in FIG. 12. For example, as shown in FIG. 12, the barrel 130 may include one or more guiding structures 134 that cooperates with a first guiding structure 122 on the instrument 120 in order to engage the instrument 120 to the holster 133, so as to direct the movements of the instrument 120 and/or end tool 140 during insertion into or removal of the end tool 140 from the holster 133.

When the end tool 140 is inserted into the barrel 130 and rotated, for example, such as was previously shown and described with respect to FIGS. 3-7, the tool retention element 134 engages the end tool 140 via tool retention structure 163 (see, e.g., FIG. 7 and further description below with regard to FIGS. 13-16), preventing the end tool 140 from being removed from the holster 133 without deliberately disengaging the end tool 140. In particular, when the end tool 140 is inserted into the barrel 130, and both are rotated to disengaged position, the a portion of the end tool 140, a securing structure 144, abuts a retaining element 125 (see FIG. 9). The retaining element 125 serves as a mating surface for mating with a portion of the securing structure 144. Because the securing structure 144 abuts the retaining element 125, the end tool 140 may not be pulled axially in the direction A'.

FIG. 11 is a detailed perspective and partial sectional view of an example rear-actuated end tool 140 engaged with an instrument 120. In FIG. 11, the instrument 120 includes one or more guiding structures 122, such as a guide protrusion, and one or more securing structures 127, such as one or more raised end portions on tines 126, which cooperate with a securing structure 144, such as a clip, located on the end tool 140, to define a releasable engaging mechanism to secure or release engagement of the instrument 120 with the end tool 140. According to various aspects of the current invention, the guiding structure 122 of the instrument 120 cooperates with a corresponding guiding structure 134 located in the barrel 130, described further below with respect to FIGS. 12-15, to guide the instrument 120 into/out of the barrel 130 upon collecting or depositing the end tool 140. For example, the guiding structures 122 and 134 may include corresponding surfaces that slidably engage one another to direct a motion of insertion or withdrawal with respect to the barrel 130. The end tool 140 may include a tube 142 (see, e.g., FIG. 11) on which the second securing structure 144 can be mounted in order to engage the first securing structure 126 of the instrument 120 to secure the end tool 140 to the instrument 120. In some aspects, for example, the securing structure 144 of the end tool 140 may include a biasing portion 143 and a front latch 145, which cooperatively bias the motion of the securing structure 144 relative to the securing feature 127 of the instrument 120, in order to allow inserting, retention and release of the end tool 140. Additionally, the securing structure 126 may interact with a corresponding feature of the barrel 130, which will be described further below.

Figure 13:
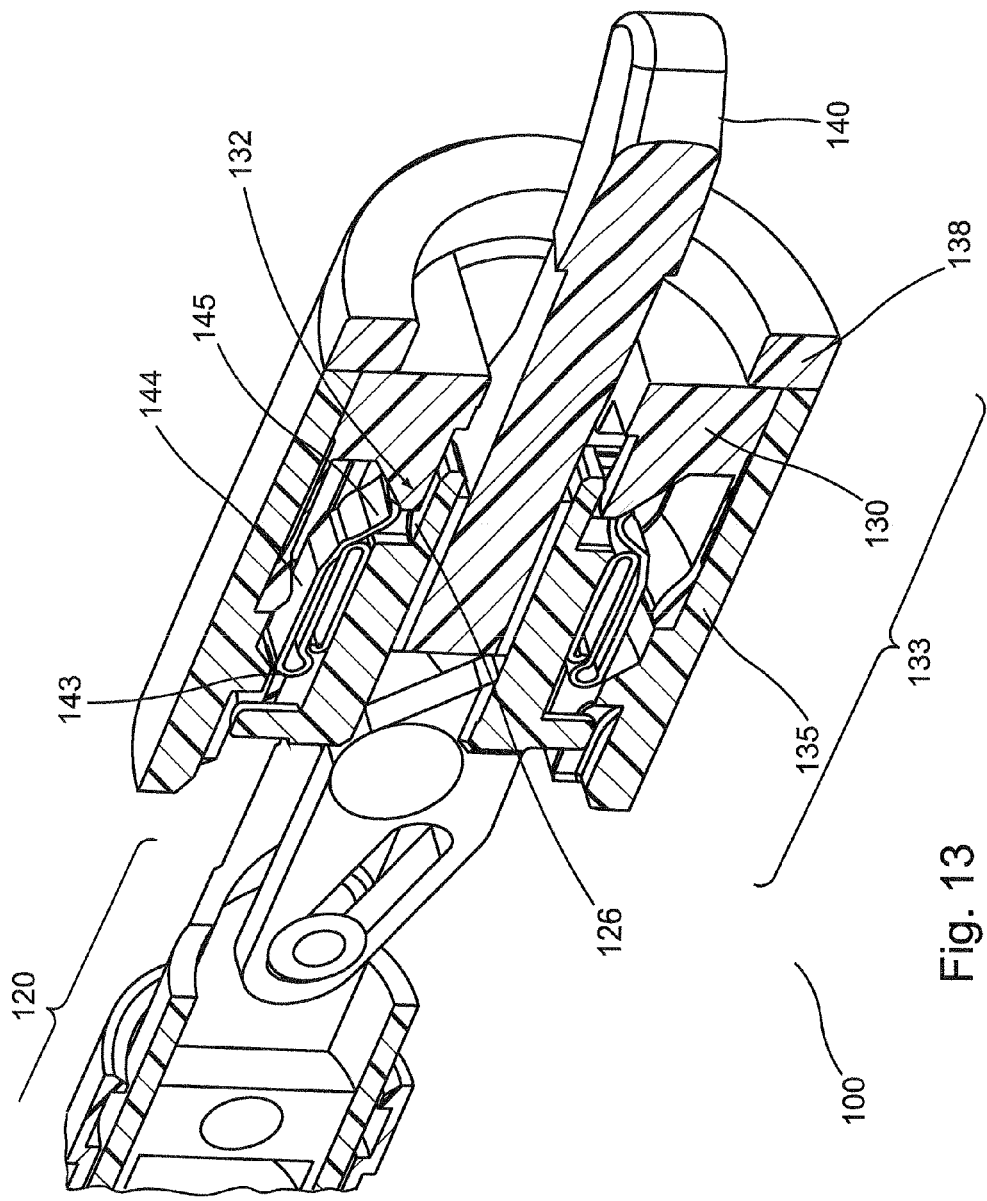
FIG. 13 illustrates a perspective and sectional view of aspects of the instrument of FIG. 6.

Portions of the barrel 130 and the releasing structure 132 of the holster 133 are illustrated in FIG. 13. In one variation, as shown in FIG. 13, the releasing structure 132 includes a surface 111 that progressively rises in the direction of movement of the end tool 140 when the end tool 140 is in process of being secured in the holster 133. According to various aspects, once the latch 145 of the end tool 140 is displaced sufficiently (e.g., in a direction away from the securing structure 126), the securing structure 144 of the end tool 140 becomes disengaged enough from the securing structure 126 of the instrument 120 so as to allow the removal of the instrument 120, by virtue of the displacement of the latch 145 being sufficient for the securing feature 127 to pass it.

A perspective and partial sectional view of these elements is provided in FIGS. 6 and 7, which illustrates the second guiding structure designed to receive the first guiding structure 122, direction of rotation B relative to the tool accommodator 135, and other features to allow the instrument 120 and first guiding structure 122 to be removed from the holster, while the end tool remains retained within the holster.

Figure 14:
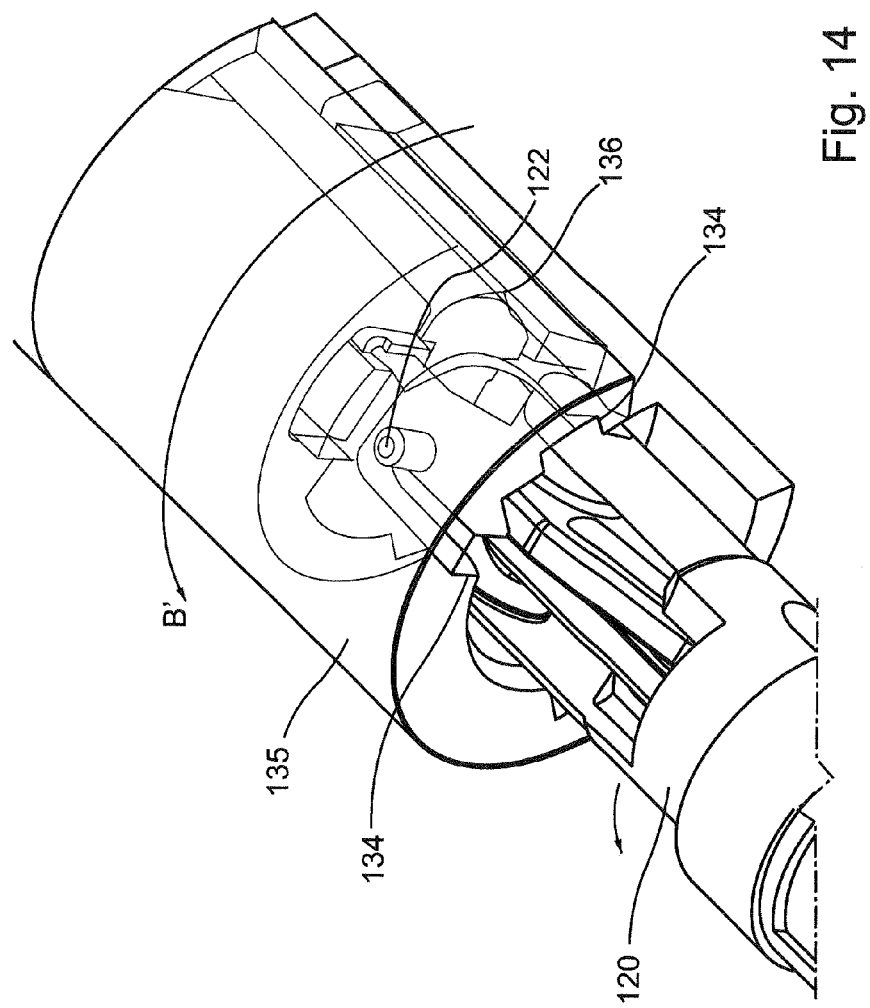
FIG. 14 shows perspective views of various features of a rear-actuated dual inter-engaging system that include a tool exchange device, in accordance with aspects of the current invention.
Figure 15:
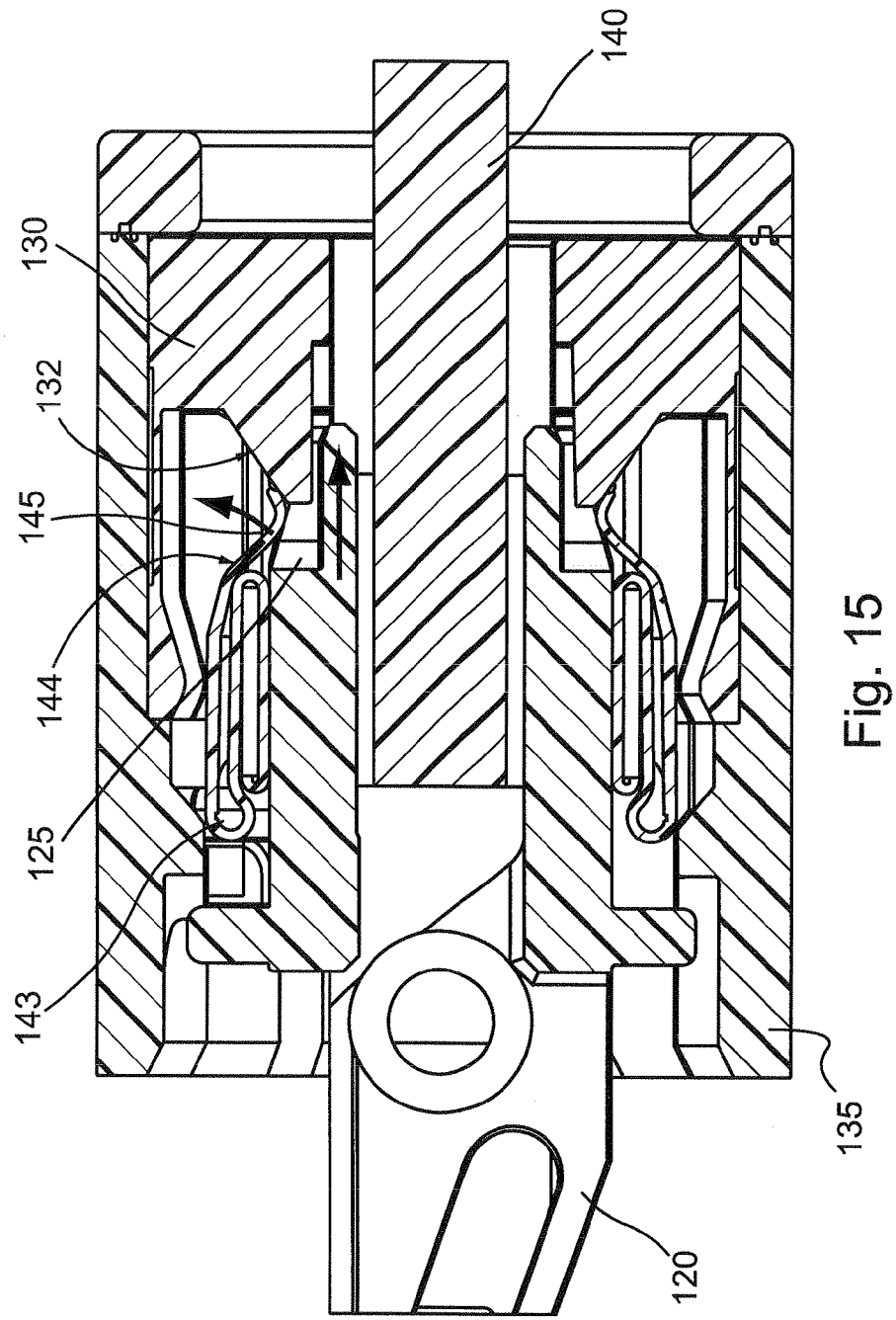
FIG. 15 is a sectional view of the engagement of an end tool with the housing of FIG. 6 upon insertion of the instrument in the tool exchange device and engagement of the end tool.

In FIG. 14, as the instrument 120 is rotated inside the holster, the guiding structure 122 of the instrument 120 also rotates, slideably travelling within guiding structure 134 of the tool accommodator 135. Following rotation, the instrument 120 may then be removed entirely from the housing 135 while leaving the end tool 140 secured by the tool accommodator 135 because in the rotated position the securing structure 144 of the end tool 140 abuts the retaining element 125. FIG. 15 illustrates travel of the latch 145 occurring during rotation of the instrument 120 inside the housing 135, and FIG. 16 illustrates various aspects of the instrument 120 at the point of removal from the tool accommodator 135.

Operation of First Example Variation

The operation of the example tool exchange system shown in FIGS. 3-16 will now be described. First, the process of separating the end tool 140 from the instrument 120 will be described. Starting from the engaged position, wherein the end tool 140 is connected to the instrument 120, the operator moves the combined structure 120, 140 towards the tool exchange device 133 along the linear path 2000 in the direction of A. The combined structure is positioned such that the guiding structures 122 line up with the corresponding guiding structure 134 (FIG. 12). The corresponding guiding structure 134 may be curved (FIG. 9), for example, so that, as the guiding structure 122 moves along the corresponding guiding structure 134 due to continued motion in the direction A, a rotational motion B is imparted on the combined structure 120, 140. Contemporaneously with this motion, the barrel 130 rotates along motion B within the tool accommodator 135. Also contemporaneously, during this motion, the front portion of latch 145 may come into contact with the ramp face 111 (FIGS. 8, 13, 15, 16) of the barrel 130.

Figure 16:
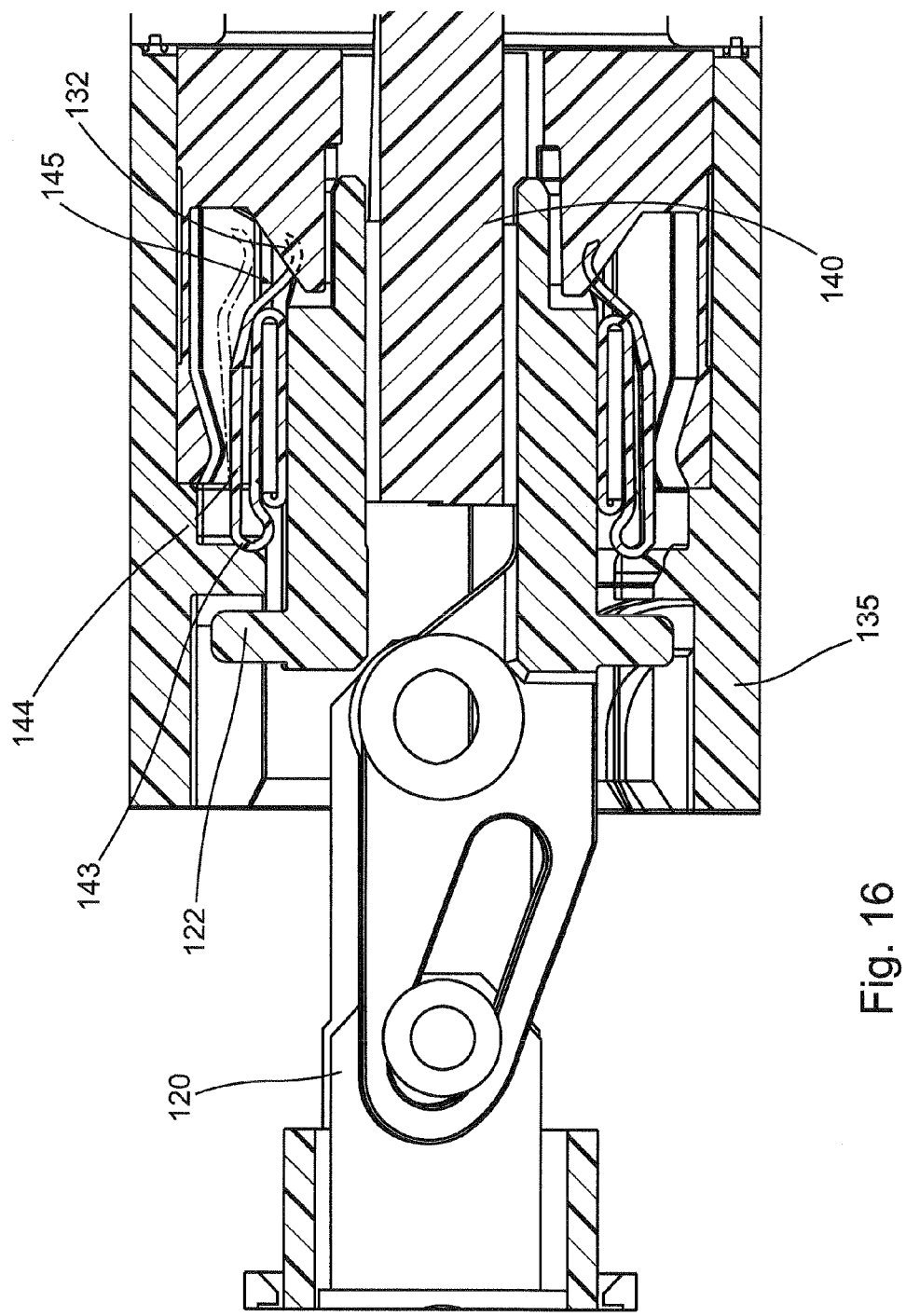
FIG. 16 shows a perspective view of portions of the rear-actuated dual inter-engaging system of FIG. 15 upon insertion of the instrument in the tool exchange device and engagement of the end tool.

As the combined structure 120, 140 continues to move along direction A, the latch slideably moves up the ramp face 111, causing the latch to unlatch from the securing feature 127 of the instrument 120 (FIG. 16). Once the combined structure 120, 140 has been full inserted and rotated by following the path provided by the corresponding guiding structure 134, the latch 145 is open. Furthermore, because the barrel 130 rotates relative to the tool accommodator 135, in the final position, the back of the securing structure 144 is blocked by a retaining element 125 of the tool retaining mechanism 135 (FIG. 9). Thus, at the fully inserted/rotated position, the latch 145 is both open and blocked from being moved in the direction A'. At this point, the operator applies a pulling force on the instrument 120 in a direction A'. Because the latch 145 is unlatched and blocked from movement in the direction A', but the instrument is not blocked from movement, the pulling force will move guiding structure 122 out of the other end of the corresponding guiding structure 134 along with the instrument 120. The tool end 140 remains trapped in the tool retaining mechanism 135 with the latch 145 resting on the ramp face 111.

Next, the process of engaging the instrument 120 with the end tool will be described. Starting from the last position described above, wherein the end tool 140 is located within the retaining mechanism 135 and the latch is open and resting on the ramp 111, the operator moves the instrument in the direction A (FIG. 6). The operator inserts the guiding structure 122 into the corresponding guiding structure 134, at the point that previously served as an exit in the above described de-coupling operation. As the guiding structure 122 moves along the corresponding guiding structure 134 in the reverse path of the de-coupling process, the tines 126 will enter the securing structure 144. As the corresponding guiding structure is further followed (FIG. 9), the combined, but unlatched, structure 120, 140 will rotate in the direction B' while moving toward A' along with the barrel 130, thereby freeing the securing structure 144 from the retaining element 125. As the combined structure 120, 140 moves in the direction A', the barrel 130 rotates so that the back of the latch 145 is no longer being blocked from axial movement. Once fully rotated, the unlatched latch 145 will slide down the ramp face 111 when the instrument is pulled in axial direction A'. As the latch 145 slideably follows the ramp face 111, the latch 145 latches to the tine 126 (FIG. 16) of the end effecter. Finally, a pulling force is provided in the direction A' to move the guiding structure 122 out of the guiding structure 134. Because the end 120 is latched to the instrument 140, the combined structure 120, 140 will exit from the tool retaining mechanism 135 as a unit.

Second Variation of Rear-actuated Dual Inter-engaging System

Figure 17:
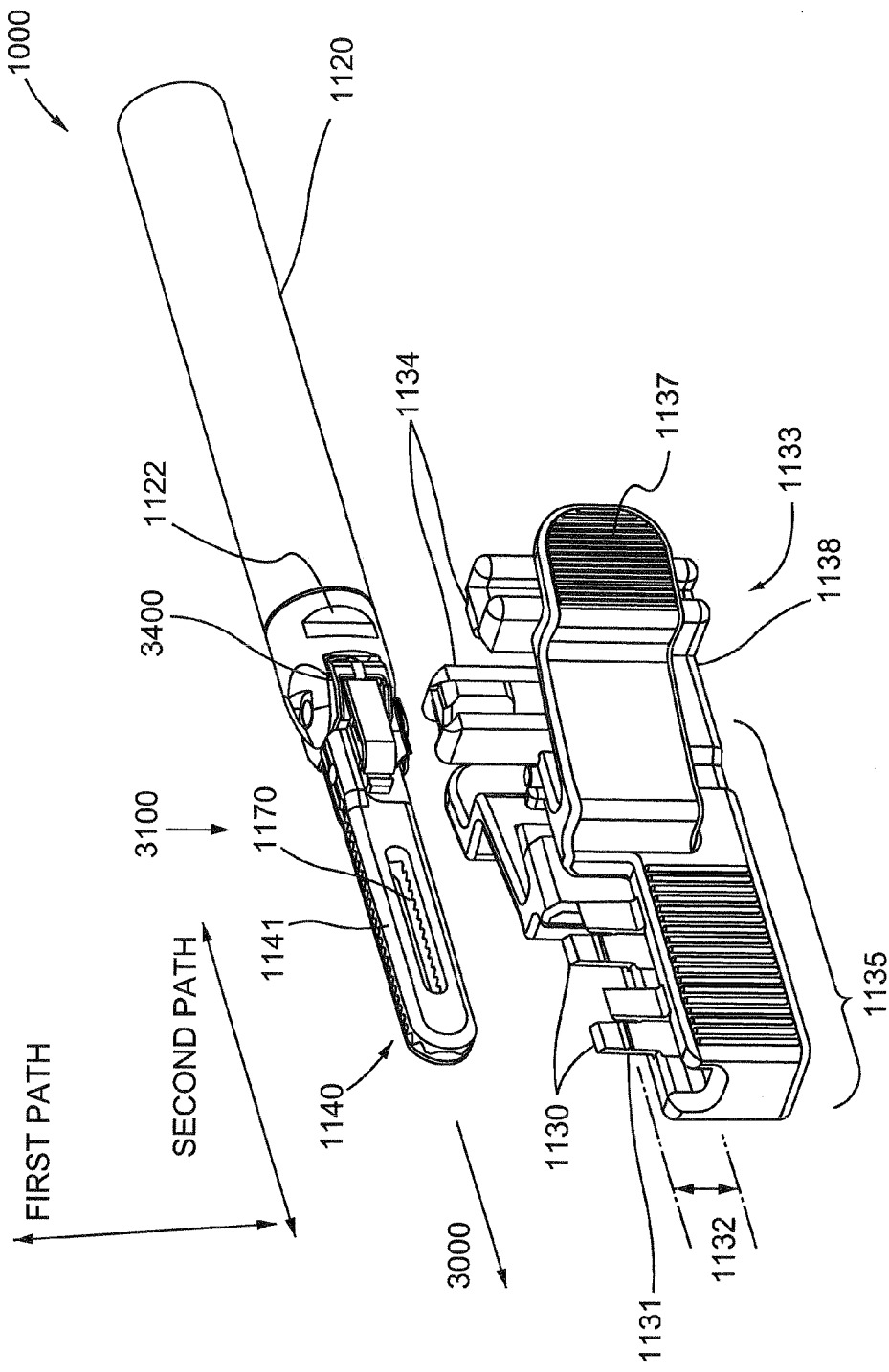
FIG. 17 shows perspective views of various portions of another example of a front-actuated dual inter-engaging system, including a tool exchange device, in accordance with aspects of another variation of the current invention.
Figure 18:
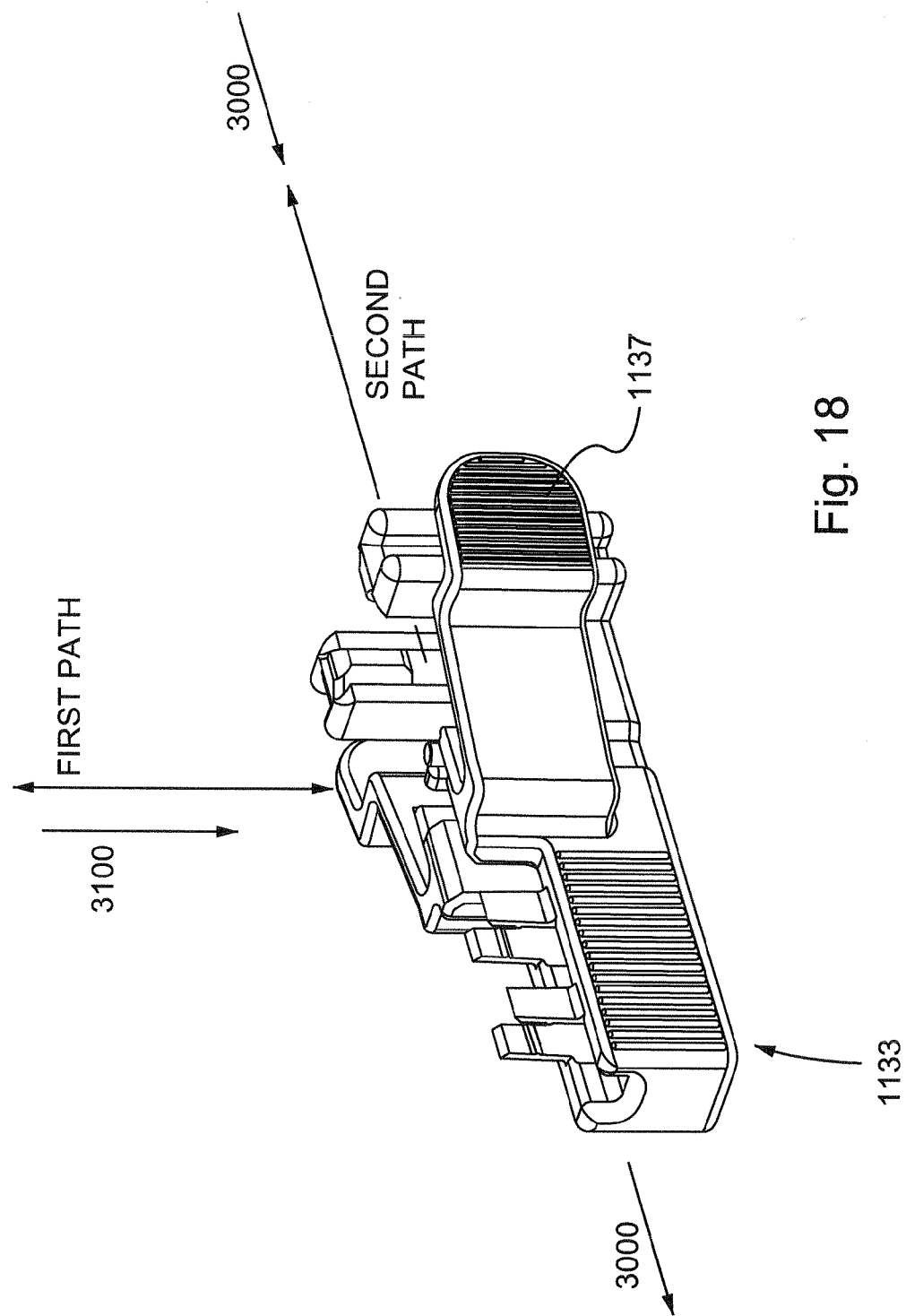
FIG. 18 show a perspective view of an example tool exchange device portion of the system of FIG. 17.
Figure 19:
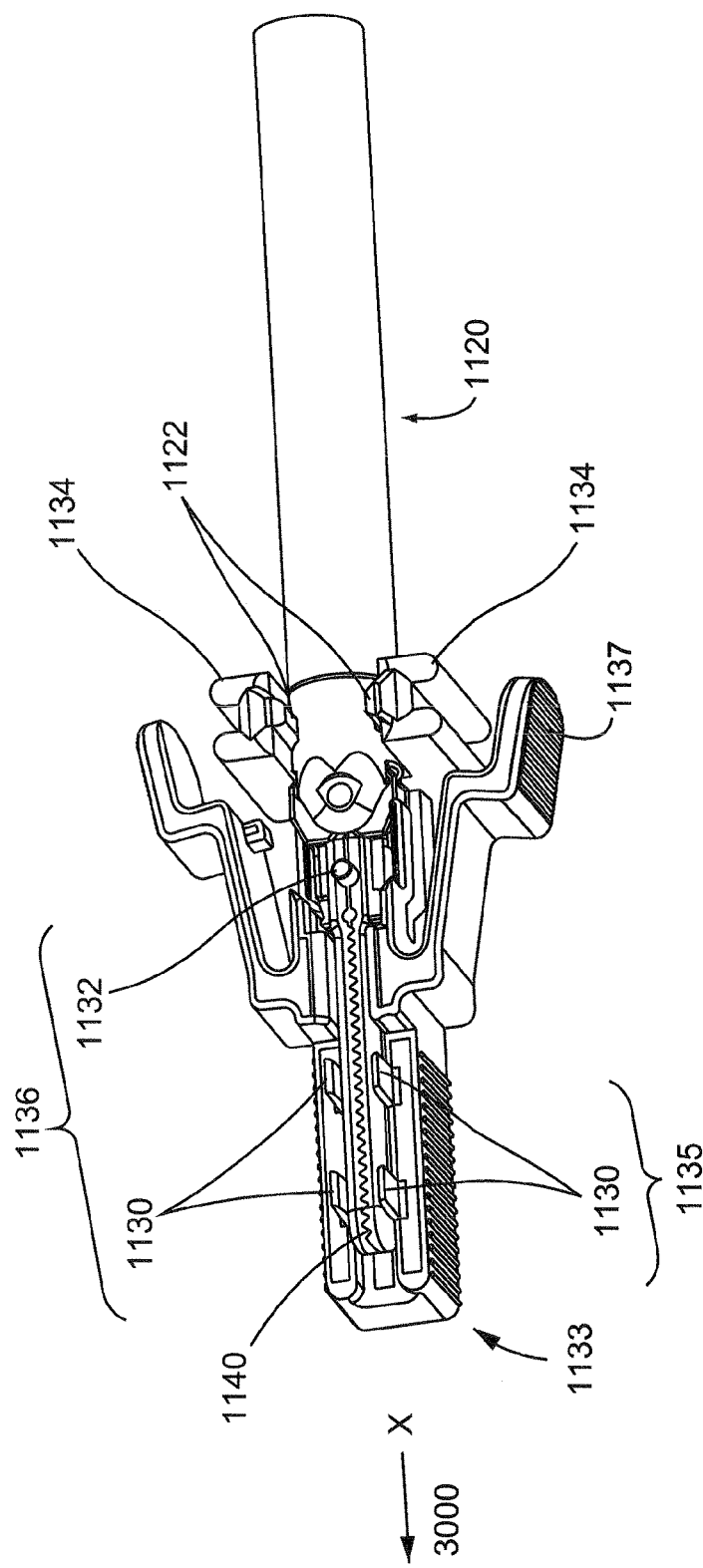
FIG. 19 shows a perspective view of the components of the system of FIG. 17, with example end tool and instrument portions in an engaged position with the tool exchange device portion.
Figure 20:
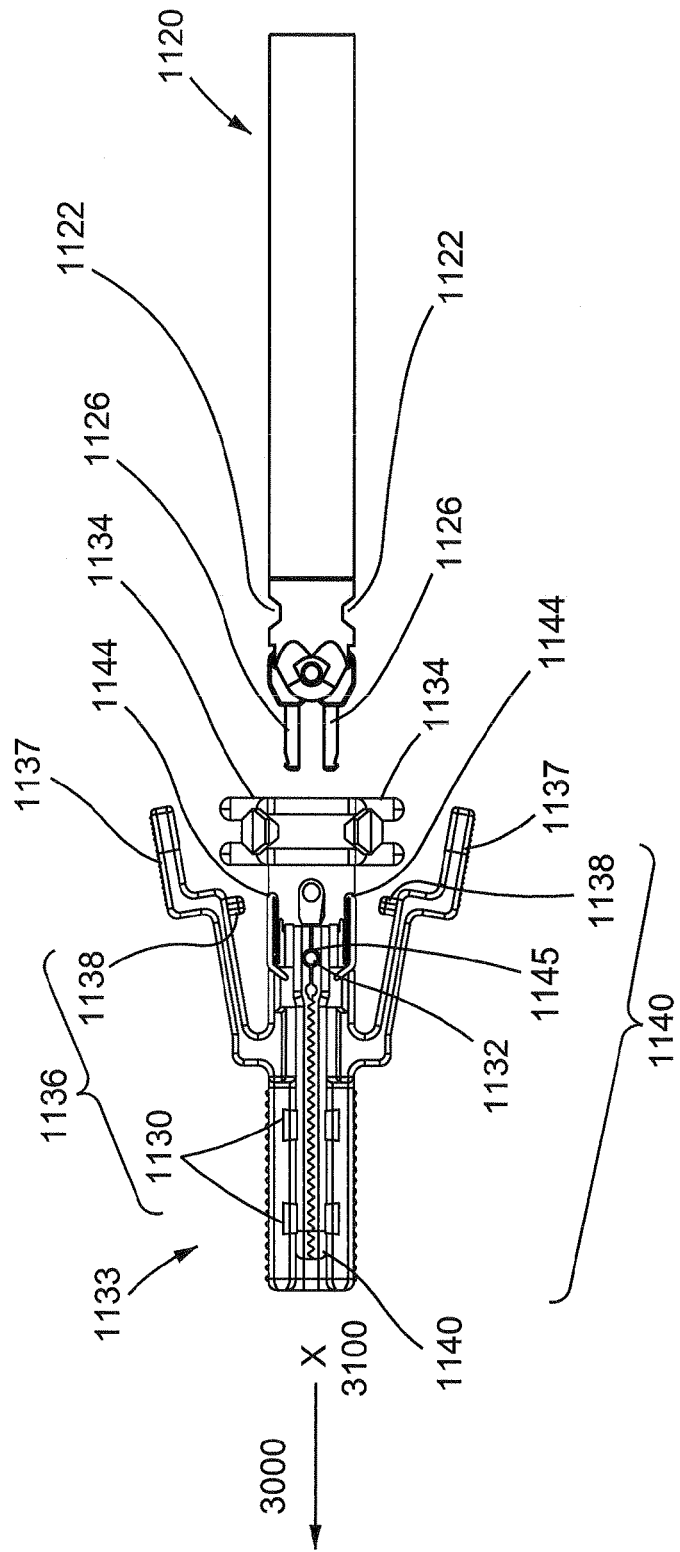
FIG. 20 is a side view of the system of FIG. 17, with the instrument portion shown disengaged from the example end tool portion, which in turn is engaged with the tool exchange device portion.

Referring to FIGS. 17-27, according to another example aspect of the current invention, a tool exchange system 1000 includes an operating instrument 1120 that is releasably connectable to an end tool 1140, which is releasably securable to a tool exchange device 1133 via a tool retaining mechanism 1135. FIG. 17 is a perspective overview of various components of another example rear-actuated dual inter-engaging system that includes a tool exchange device, according to yet other aspects of the current invention. FIG. 18 shows the tool exchange device relative to various paths of motion, in accordance with aspects of the present invention. FIG. 19 is a perspective overview of the rear-actuated dual inter-engaging system of FIG. 17 upon insertion of the instrument in the tool exchange device and engagement of the end tool. FIG. 20 is another perspective overview of a rear-actuated dual inter-engaging system of FIG. 17 upon disengaging the end tool and removing the instrument from the tool exchange device.

As shown in FIGS. 17 and 18, the engaging and disengaging of the end tool 1140 with the tool exchange device 1133 may be accomplished by moving the instrument 1140 and end tool 1140 sequentially along two motions, as shown in FIG. 18, along a first path 3100 and a second path 3000. Note that each motion is bi-directional and the two directions may be used to perform engaging and/or disengaging operations as further described below.

Moving the instrument 1120 along a first direction in the first path 3100 and then the second direction in a second path 3000 will: 1) engage the end tool 1140 with the tool exchange device 1133 via tool engaging features 1136, 2) enable the end tool 1140 to be disengaged from the instrument 1120, and 3) allow the instrument 1120 to be disengaged from the end tool 1140. Moving the instrument 1120 in the reverse sense, i.e., along the opposite direction in the second path 3000 and then the opposite direction in the first path 3100 will: 1) engage the instrument 1120 with the tool exchange device 1133 via the operating instrument engaging system 1131, 2) allow the end tool 1140 to be engaged with the instrument 1120, and 3) allow the instrument 1120 with the engaged end tool 1140 to be removed as a unit.

Specifically, the end tool 1140 may be engaged via a tool exchange system 1000 by engaging a tool engaging features 1136, as follows. First, in FIG. 17, the end tool 1140 is shown above the tool exchange device 1133. The operating instrument engaging system 1131 may be disengaged by moving the instrument 1120 and engaged end tool 1140 to a releasing position as shown in FIG. 19. For example, in FIG. 17, the end tool 1140 engaged with the instrument 1120 may be moved downwardly, as shown (along a first path 3100) to engage the tool exchange device 1133, reaching the position shown in FIG. 19. Upon reaching an end tool releasing position, the instrument 1120 engaged with end tool 1140 may be then moved along the second direction 3000 in substantially the reverse direction of engagement, to reach the position shown in FIG. 20. While the instrument 1120 is moved along this second direction 3000, the end tool 1140 is released from the instrument 1120. Moving the instrument 1120 along this second direction 3000 also disengages the operating instrument engaging system 1131. Subsequently, the instrument 1120 is removed from the tool exchange device 1133. Since the tool engaging system 1136 remains engaged, the end tool 1140 remains engaged and within the tool exchange device 1133.

Figure 21:
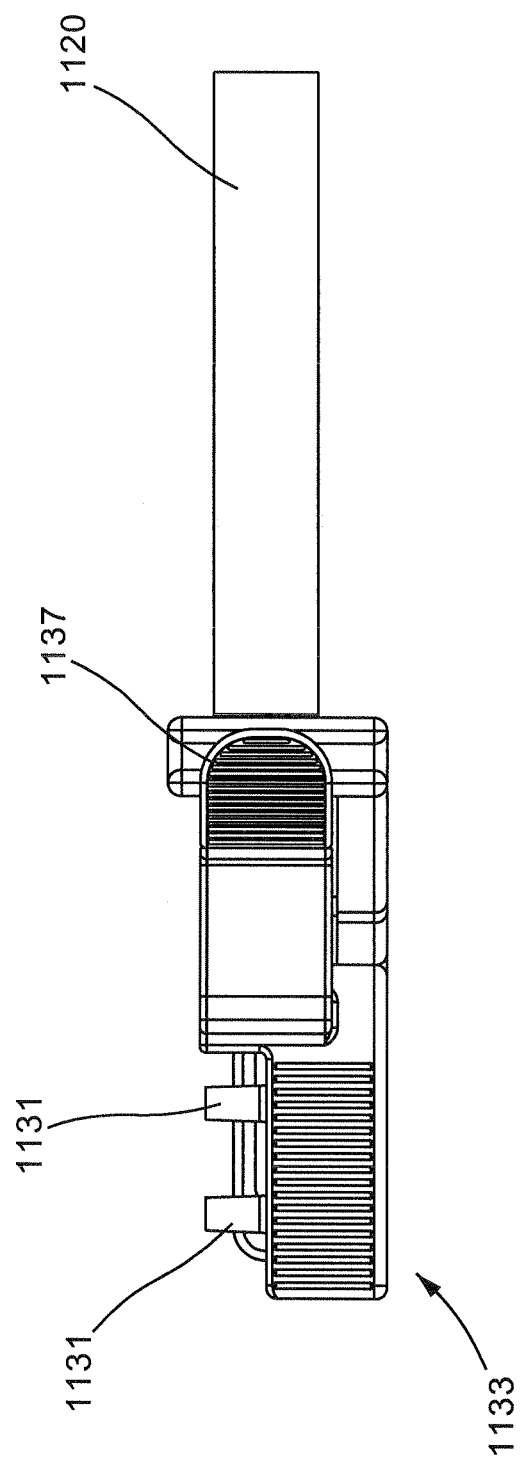
FIG. 21 is a profile view of the system of FIG. 17 with the instrument and end tool portions in an engaged position with the tool exchange device portion.

The process of retrieving an end tool 1140 that is engaged to the tool exchange system 1000 is substantially the reverse of the process described in the previous paragraph and may proceed as follows. First, the instrument 1120 is brought into contact with the end tool 1140 within the tool exchange system by moving the instrument 1120 in direction 3000, as shown in FIGS. 17 and 21, reaching the position of FIG. 19, upon which end tool 1140 is then connected to the instrument 1120. Subsequently, the instrument 1120 and engaged end tool 1140 may be translated along the first path 3100 (e.g., out of the page) so as to disengage the instrument 1120 with engaged tool end 1140 from the tool exchange device 1133.

The tool exchange system 1000 may include a tool retaining mechanism 1135 within the tool exchange device 1133. The tool retaining mechanism 1135 may, for example, include retention elements 1130, which is a mating surface that may engage or mate with structure portion of the end tool, and a connection element 1132, for effecting travel along a path defined by a pin-shaped extension.

The tool engaging device 1131 may include one or more instrument guide elements 1134 that cooperate with a guide structure 1122 (see, e.g., FIG. 19) of the instrument 1120 in order to engage the instrument 1120 with the tool exchange device 1133 and, more generally, direct the movements of the instrument 1120 and/or end tool 1140 when inserted into or removed from the tool exchange device 1133.

In general, the instrument 1120 may be reversibly coupled to the end tool 1140 through a series of securing structures, as shown in FIG. 20. For example, the instrument 1120 may include securing structures 1126 that cooperate with securing structures 1144 on the end tool 1140 to releasably secure the end tool 1140 with respect to the instrument 1120. For example, in one aspect, the securing structures 1126 of the instrument 1120 may include a nodule for receiving the securing structures 1144 of the end tool 1140, which include a clip and latch mechanism. The clip and latch mechanism may be sized such that the securing structures of the instrument 1120 accept the latch to reversibly secure or release the end tool 1140 with respect to the instrument 1120.

Referring to FIG. 19, the tool engaging device 1133 of the variation of the rear-actuated dual inter-engaging system shown includes retention elements 1130 for engaging corresponding structure portions of the end tool 1140 and a connection element 1132, designed to receive a pin-shaped extension, which may work together to engage the end tool 1140.

Retention elements 1130 for engaging the retention structure 1140a of the end tool 1140, among other things, may snap to, curl around or otherwise clasp an edge of the end tool 1140, as shown in FIG. 19. Five retention elements 1130 for engaging the retention structure 1140a of the end tool 1140, for example, may be included in the tool engaging device 1133. Alternatively, there may be any other suitable number of retention elements 1130 for retaining the end tool 1140. Retention elements 1130 for engaging the retention structure 1140a of the end tool 1140 may be, for example, in the shape of barbed posts, as shown in FIG. 17. Other possible shapes include those of pins, clips hooks or keys. The fastening portions may comprise similar material to the tool exchange device 1133, which may include, for example, molded plastic. However, it may be advantageous in certain variations for the retention elements 1130 to comprise another material that may, for example, reinforce the retention elements 1130 or increase their elastic properties. Examples of such materials include, but are not limited to: metals, plastics, various elastomeric polymers and combinations thereof.

Typically, the retention elements 1130 for engaging the end tool 1140 prevent lateral motion (e.g., motion in the direction perpendicular to directions 3000 and 3100) when the end tool 1140 is placed in the tool exchange device 1133. Once the retention elements 1130 for engaging the end tool 1140 snap to, curl around, or otherwise clasp an edge of the end tool 1140, as shown in FIG. 19, the retention elements 1130 for engaging the end tool 1140 restrain vertical motion of the end tool 1140. More specifically, interaction between the retention elements 1130 for engaging the end tool 1140 and portions of the end tool 1140 interact to restrain motion of the end tool 1140 along the direction of the first path 3100 shown in FIG. 18. This restraint decreases the chance that the end tool 1140 can be inadvertently dislodged from the tool exchange device 1133 during use. For example, if the instrument 1122 remains connected to the end tool 1140, as shown in FIG. 19, and force is suddenly applied to the instrument 1122, retention elements 1130 will restrain movement of the end tool 1140 and instrument 1122 so as to diminish the chance of an accidental or inadvertent dislodging of the end tool 1140 from the tool exchange device 1133.

The interaction between the retention elements 1130 and the end tool 1140 may be facilitated by one or more protruding features 1131, as shown in FIG. 17. The protruding features 1131 may have, for example, the shape of a hook or catch that clasps the upper edge 1141 (FIG. 17) of the end tool 1140. Alternatively, the protruding features 1131 may have other suitable shapes, such as rectilinear, diamond, smooth, curved or variations of any of the above described shapes. The protruding features 1131 may also engage the end tool 1140 at a position other than the upper edge 1141.

For example, the protruding features 1131 may engaged openings, depressions, or other receiving features in one or more portions of the end tool 1140. One such feature of the end tool 1140 that may interact with the protruding feature 1131 is side opening 1170, shown in FIG. 17. However, it is to be understood that the interaction between the retention elements 1130 and the end tool 1140 may be accomplished in any suitable manner to restrict the lateral and vertical motion of the end tool 1140 when it is engaged with the tool exchange device 1133.

As shown in FIG. 17, the protruding features 1131 may be positioned on the retention elements 1130 for engaging the end tool 1140, such that they engage the end tool 1140 when it reaches a specific position, such as the engaging/releasing position shown in FIG. 19.

Figure 22:
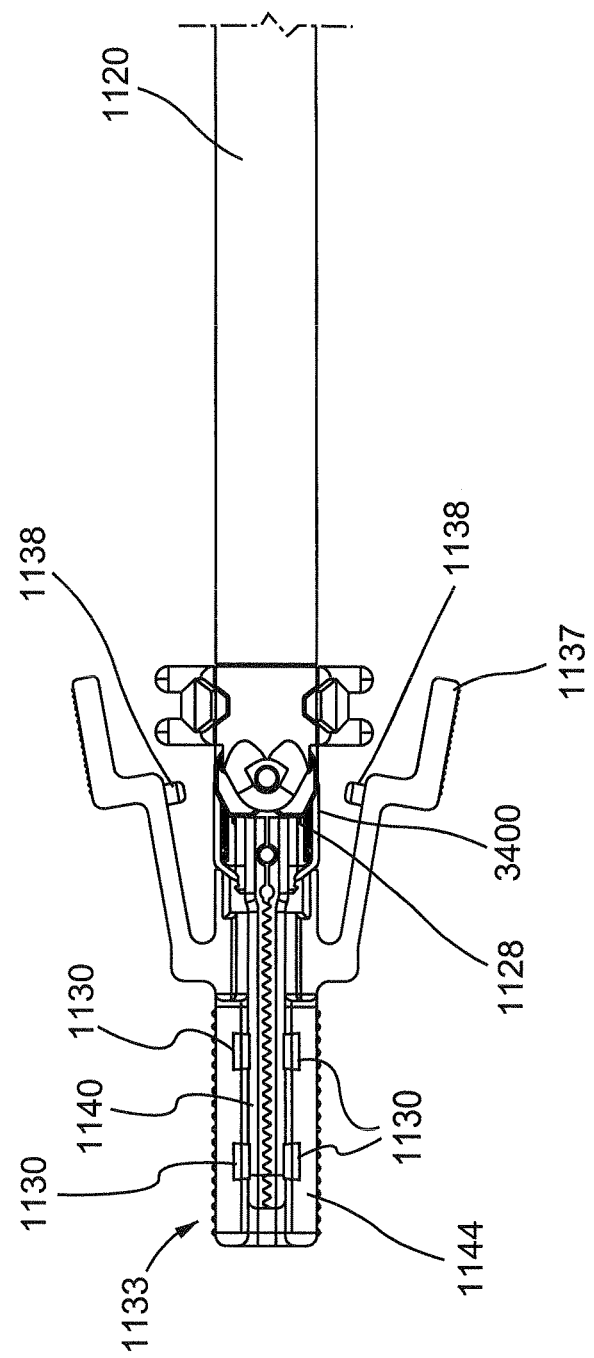
FIG. 22 is a side view of the system of FIG. 17 with the instrument and end tool portions in an engaged position with the tool exchange device portion.

FIG. 21 is a profile view of retention elements 1130 for engaging the end tool 1140 when the end tool 1140 is in the engaging/releasing position shown in FIG. 19. As shown in FIG. 20, the releasing position allows the tool release mechanism 1137 having projecting member 1138 to engage connection element 1132, which activates the securing structure 1144 on the end tool 1140. As shown in FIGS. 17 and 22, a connection element 1132 may be positioned such that it may engage the release 1128 only when the end tool 1140 is in the releasing position shown in FIG. 19. Therefore, the tool release mechanism 1137 (FIG. 22) cannot release the end tool 1140 from the instrument 1120 until the retention elements 1130 for engaging the retention structure 1140*a* of the end tool 1140 have engaged the end tool 1140 and engaged it to the tool exchange device 1133, as described above.

As further shown in FIGS. 20-22, one function of the securing structure 1144 in the tool release mechanism 1137 is to release the end tool 1140 from the instrument 1120. This can be accomplished by a variety of components and it is to be understood that the description that follows is merely illustrative. The instrument 1120 may connect to the end tool 1140 via connection structure 1126, which may be designed to fit reversibly into accommodating slots in the end tool 1140. The securing structure 1144 may function as a pivotable clip that applies pressure to the connection structure 1126. When the tool release tabs 1128 (see, e.g., FIG. 22) are engaged, an internal pressure is applied to the connection structure 1126 sufficient to prevent release of the instrument 1120 from the end tool 1140. To release the tool release tabs 1128, an external pressure is applied at position 3400 (FIGS. 17, 20 and 22) that pivots the tool release tabs 1128 in such a way to release this pressure. External pressure may be applied, for example, to the tool release tabs 1128 via the connection elements 1132 and the tool release mechanism 1137 (see, e.g., FIG. 22).

The connection element 1132 of the tool engaging system 1136, among other things, may include features that snap to or otherwise fitably engage a guide structure 1145. A single connection element 1132 may be provided in the tool engaging system 1136, as shown in FIG. 19. Alternatively, there may be any other suitable number of pin or other guide/snap receiving features included in connection element 1132. The connection element 1132 may also comprise the same or similar material as that in the retention elements 1130 for engaging the retention structure 1140*a* of the end tool 1140, the tool exchange device 1133 or both. Alternatively, the connection element 1132 may be made of a harder material, such as a hardened metal, in order to decrease movement of the end tool 1140 once the tool engaging system 1136 is engaged. The connection element 1132 may have one of a number of different shapes including a cylindrical shape, as shown in FIG. 19, as well as the shape of a cone, sharpened cylinder, rod or a rectilinear shape, for example.

The connection element 1132 of the end tool engaging system 1136 may engage the end tool 1140, as shown in FIG. 19 when the end tool 1140 is placed in the tool engaging device 1133. More specifically, interaction between the connection element 1132 and the guide structure 1145 of the end tool 1140 may restrain the motion of the end tool 1140 along the direction 3000 shown in FIGS. 17-19. This restraint decreases the chance that the end tool 1140 can be inadvertently dislodged from the tool exchange device 1133 during use.

Referring to FIGS. 17-19, the tool exchange device 1133 may include a guide structure 1122 for interacting with an instrument guide element 1134 of the tool exchange device 1133. The instrument guide element 1134 may interact with the guide structure 1122, for example, as the instrument 1120 as it is engaged with into the tool exchange device 1133 along direction 3100, as shown in FIG. 17.

The instrument guide element 1134, among other things, may engage the guide structure 1122 via features protruding from the guide element 1134 into the guide structure 1122, as shown in FIG. 19. Two instrument guide elements 1134 may be included in the tool exchange device 1123, as shown in FIGS. 17-19. Alternatively, any other suitable number of instrument guide elements 1134 may be included. Instrument guide elements 1134 may be, for example, in the shape of lateral protrusions, as shown in FIG. 17, or they may be otherwise shaped so as to interact with one or more portions of the instrument 1120. Other possible shapes include those of pins, clips hooks or keys. Generally, the instrument guide elements 1134 may comprise the same or a similar material to that of the tool exchange device 1133, which may include, for example, molded plastic. However, it may be advantageous in certain variations for the instrument guide elements 1134 to be made of another material that may, for example, reinforce the instrument guide elements 1134 or increase elastic properties.

The tool exchange device 1133, the tool release mechanism 1137, and the tool engaging system 1136 are designed to be complimentary. More specifically, the tool exchange device 1133 will not allow the instrument 1120 to be removed until the tool engaging features 1136 have engaged the end tool 1140 to the tool exchange device 1133 and the tool release mechanism 1137 has released the end tool 1140 from the instrument 1120. An example approach to accomplishing such release is via the interaction among instrument guide elements 1134 of the tool exchange device 1133, the tool release mechanism 1137, and tool engaging features 1136 is discussed below.

As shown, for example, in FIG. 17, the instrument guide elements 1134 may be positioned on the tool exchange device 1133 such that they engage guiding structures 1122 when the end tool 140 is placed in the tool exchange device 1133. As also shown in FIG. 17, the instrument guide elements 1134 may be of a length such that they no longer engage the first guiding structures 1122 when the end tool 1140 has reached the releasing position shown in FIG. 19. Thus, when the end tool 1140 has reached the releasing position of FIG. 19, the instrument guide elements 1134 may no longer be engaged with the first guiding structures 1122 of the instrument 1120, thereby permitting the instrument to move freely at least along direction 3000 (FIG. 19) except for the fact that the instrument 1120 remains engaged with the end tool 1140. Since the end tool 1140 is also fully engaged with the tool exchange device 1133 via the tool engaging system 1136 in the position shown in FIG. 20, the connection between the end tool 1140 and the instrument 1120 prevents the instrument from moving freely along direction 3000. Once the tool release mechanism 1137 (FIG. 20) is used to release the end tool 1140 from the instrument 1120, however, motion of the instrument 1120 along direction 3000 becomes possible, and the instrument may be removed, as shown in FIG. 20.

Figure 23:
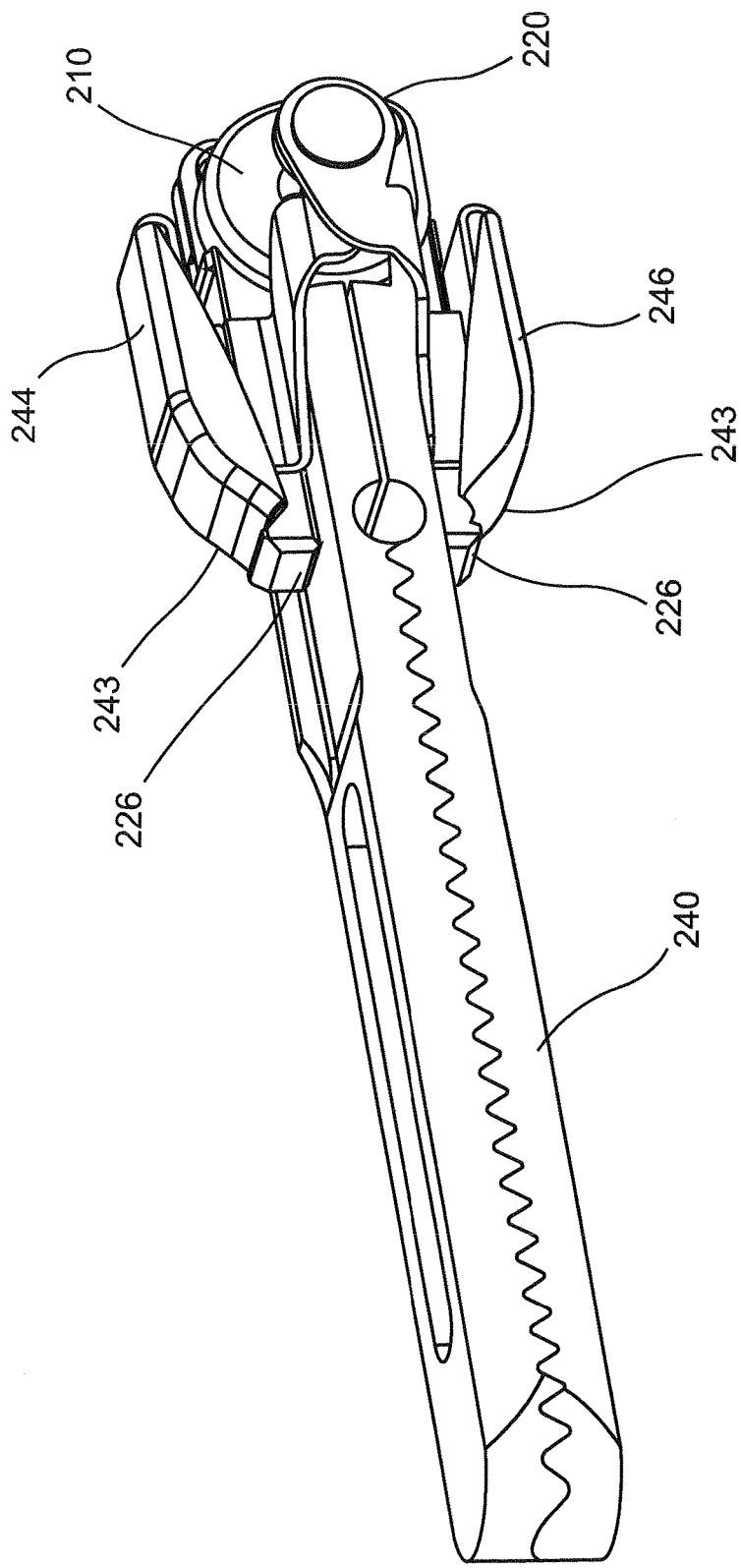
FIGS. 23-24 contain perspective views of portions of a rear-actuated dual inter-engaging system, in accordance with aspects of another variation of the current invention.
Figure 24:
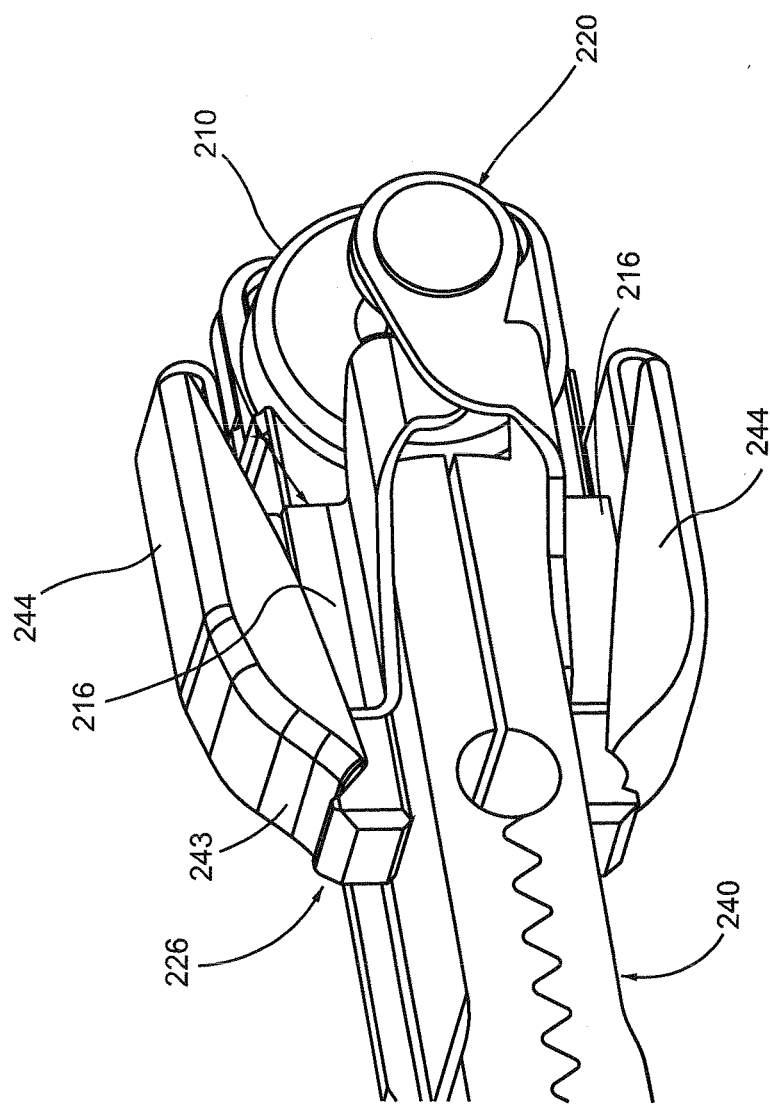

FIGS. 23-24 are perspective views of various portions of an example rear-actuated dual inter-engaging system 200, according to an example aspects of the current invention. In FIGS. 22-24, the end tool 240 is retained by clips 244 to a collecting instrument 210. According to various example aspects, a front portion 243 of a clip 244 is biased and hinges on a tine 226, the tine 226 being part of the end tool 240. Via these features, the end tool 240 is secured to the instrument 210. FIG. 24 also shows that the clip 244 may be hinged about a tube 216 on each side of the end tool 240, and both tubes 216 may be connected around a hinge pin 220 that allows movement of the tubes 216. Accordingly, the tubes 216 secure the instrument 210, and the clips 244 secure the end tool 240 to the instrument 210.

Figure 25:
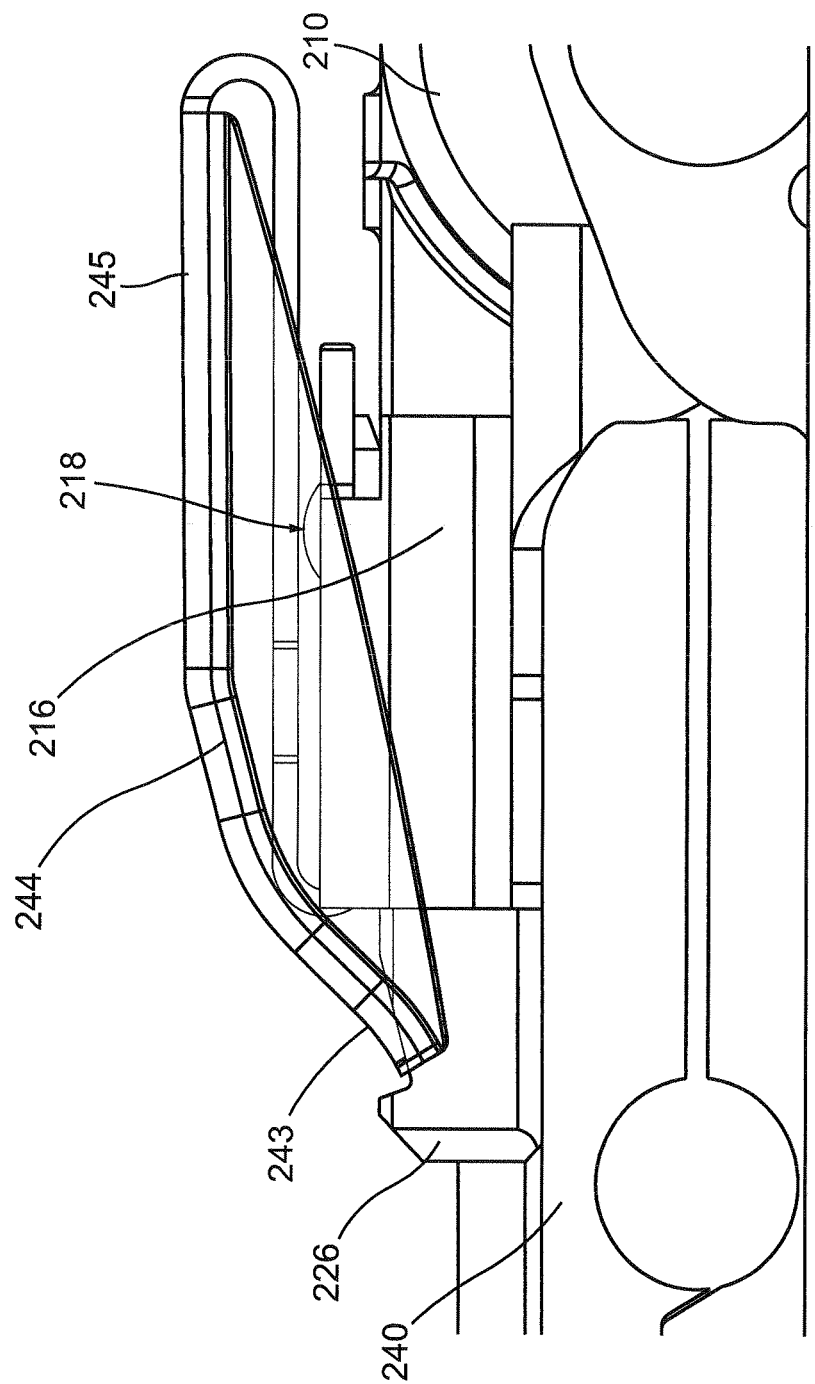
FIGS. 25-26 show side and cross-sectional views, respectively, of the rear-actuated dual inter-engaging system of FIGS. 23 and 24.
Figure 26:
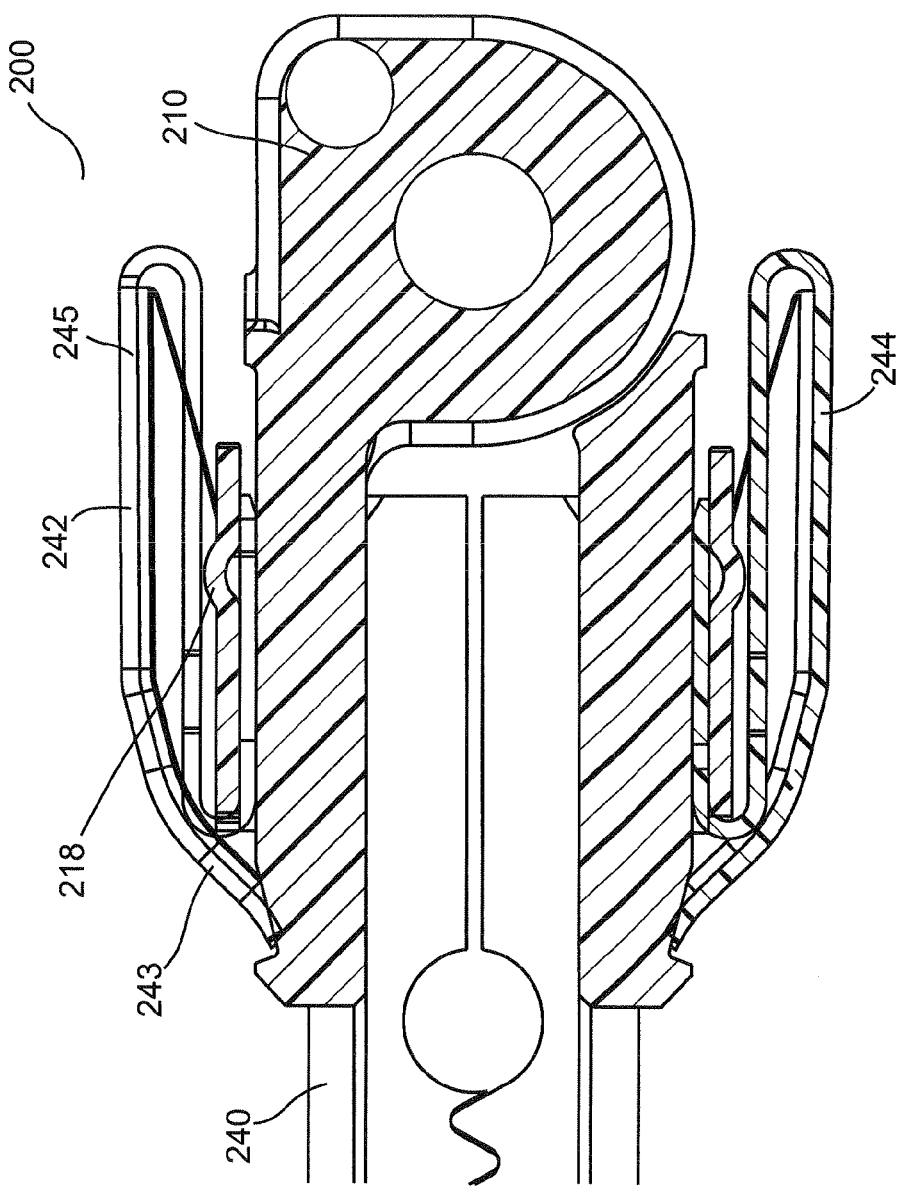

FIGS. 25-26 are side views of a rear-actuated dual inter-engaging system 200 of FIGS. 23-24, according to example aspects of the current invention. In FIGS. 25-26, a first end portion 243 of the clip 244 may be urged in and out of the tine 226 via a pressure applied to a second portion 245 of the clip 244. The pressure applied to the second portion 245 may be applied to an outer surface of the rear portion 245, for example. According to various aspects of the invention, in order for the first portion 243 to be urged out of the tine 226, the pressure being applied on the second portion 245 may be converted to pivotal movement of the first portion 243 about a pivot point 218. According to various aspects of the current invention, the pivot point 218 receives the pressure applied to the second portion 245 of the clip 244 and transfers the motion of the second portion 245 into an opposite pivoting motion of the first portion 243 of the clip 244. Thus, for example, the first portion 243 may pivot out of the groove formed by the tine 226 when a pressure is applied to the second portion 245, as shown in FIG. 25. When the first portion 243 is urged away from the tine 226, then the instrument 210 may be disengaged from the end tool 244, via linear motion of the end tool 244 and tine 243 past the end of the clip 244 near the first portion 243. As a result, the instrument 210 may thus be subsequently removed.

Figure 27:
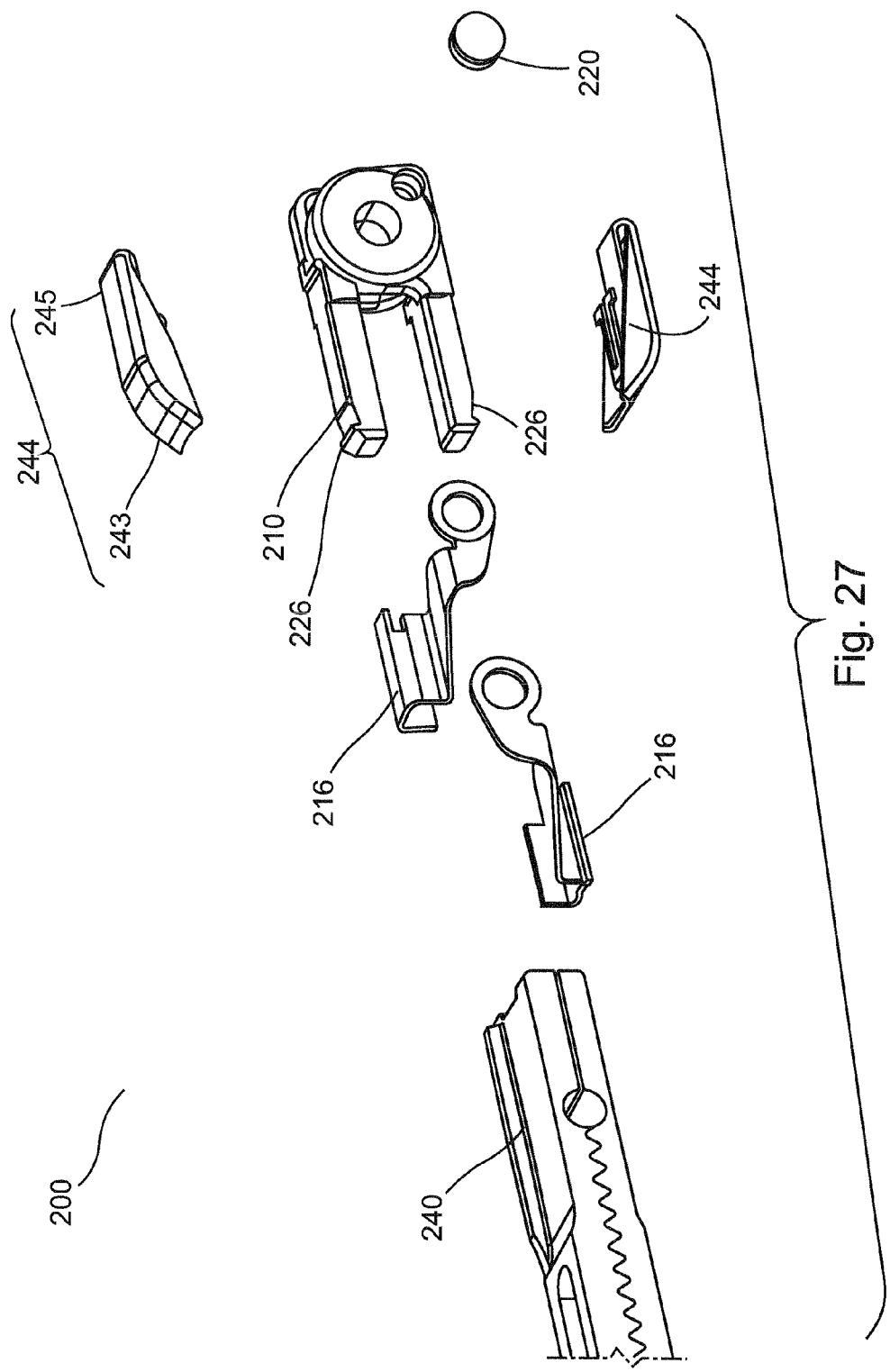
FIG. 27 is an exploded view of portions of the rear-actuated dual inter-engaging system of FIGS. 23 and 24.
Figure 28:
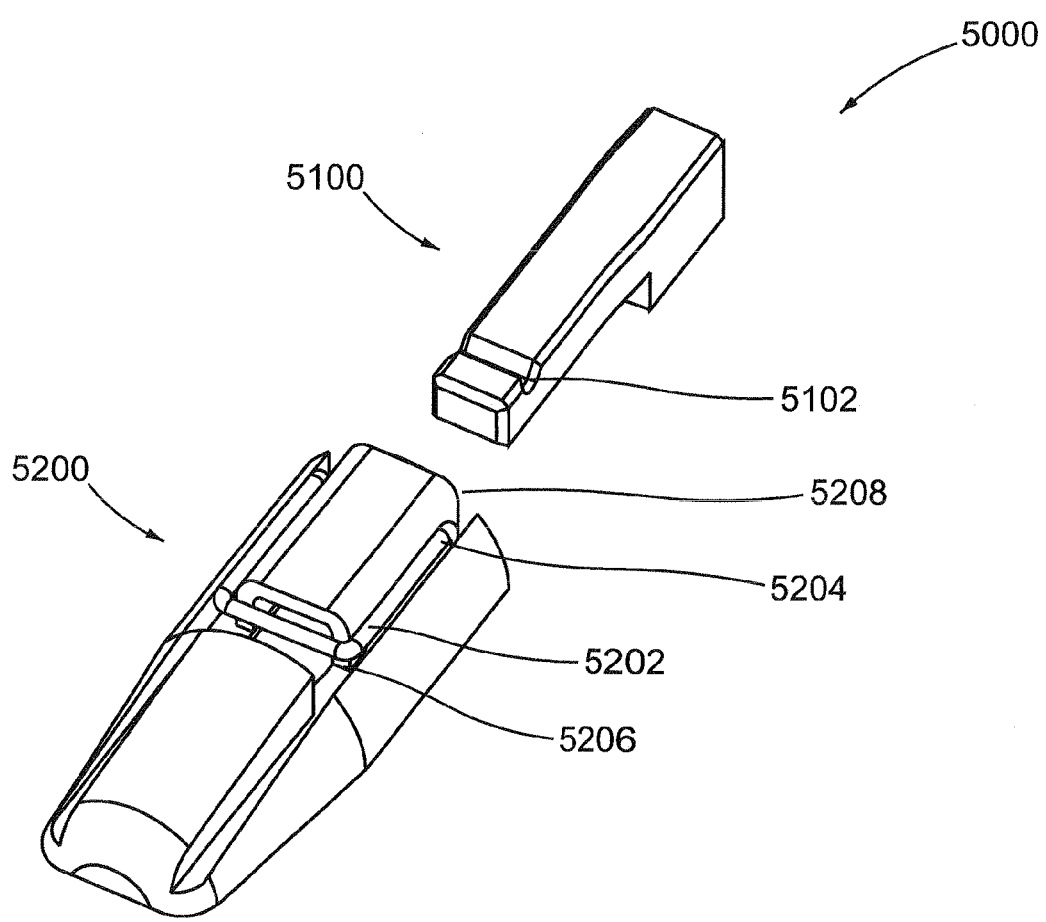
FIG. 28 is an exploded view of various portions of an example system that includes a clip retaining mechanism that may be used to engage an end tool and instrument, in accordance with aspects of another variation of the present invention.

FIG. 27 is an exploded view of a rear-actuated dual inter-engaging system 200 of FIGS. 23-26, according to example aspects of the current invention. In FIG. 28 the instrument 210 includes the tines 226, an urging device that includes the clips 244, the tubes 216 and the hinge pin 220, and the end tool 240.

Operation of Second Example Variation

The operation of the example tool exchange system shown in FIGS. 17-27 will now be described. First, the process of separating the end tool 240,1140 from the instrument 1120 will be described. Starting from the engaged position, wherein the end tool 1140 is connected to the instrument 1120, via the securing structure (or latches) 1144, the operator moves the combined structure 1120, 1140 towards the tool exchange device 1133 along the approximately linear path 3100. The combined structure is positioned such that the guiding structures 1122 line up with the corresponding guiding elements 1134 (FIG. 17). The corresponding guiding elements 1134 may be shaped so that as the guiding structure 1122 moves along the corresponding guiding structure 1134 in the direction 3100.

After the combined structure 1120, 1140 is sufficiently inserted into the exchange device 1133, the securing structure 1144 is lined up with the projecting member 1138 of the tool release mechanism 1137 (FIG. 20). Additionally, once the combined structure 1120, 1140 is inserted into the exchange device 1133, the retention elements 1130 ensure the end tool 1140 securely contained within the exchange device. Next, an operator actuates the tool release mechanism 1137 by applying pressure on the tool release mechanism towards the securing structure 1144. As pressure is applied, the projecting member 1139 may come into contact with a portion of the securing structure 1144. As pressure continues to be applied to the release mechanism 1137 via the projecting member 1138, for example the securing structure 1144 is caused to pivot about the pivot point 218 (FIG. 25). Once the securing structure 1144 is sufficiently pivoted, the tines 1125 (FIG. 20) are no longer mated with the securing structure 1144, as long as the pressure is continuously applied to the release mechanism 1137.

Contemporaneously with pivoting the securing structure 1144, an operator then pulls the instrument 1120 along the second path in the direction opposite 3000. Because the securing structure 1144 is not secured to the tines 1125, the pulling force will allow the instrument 1120 to be removed from the exchange device 1133, while the end tool 1140 remains in the exchange device.

Next, the process of engaging the instrument 1120 with the end tool 1140 will be described. Starting from the last position described above, wherein the end tool 1140 is located within the exchange mechanism 1135, the operator moves the instrument in the direction of 3000. The operator inserts the tines 1126 into the end tool 1140, which engages the tines 1126 with the securing structure 1144 of the end tool 1140. After the end tool 1140 and the instrument 1120 are mated via the securing structure 1144, the operator moves the combined structure 1120, 1140 in the direction along the first path in the direction opposite of 3100 until the combined structure 1120, 1140 is free from the exchange device 1133.

Clip Retaining Mechanism

Figure 29:
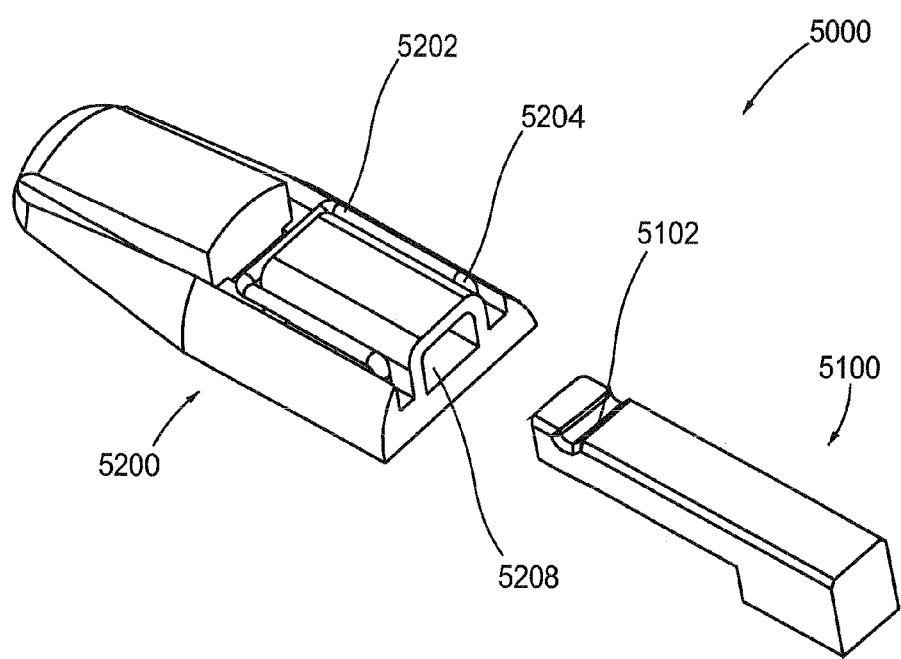
FIG. 29 is a perspective view of portions of the system of FIG. 28.

FIG. 28 is an exploded view of a system 5000 including a clip retaining mechanism that may be usable to engage an end tool and instrument in one or more of the variations described herein. FIG. 29 is a perspective view of the system of FIG. 28. More specifically, the system 5000 includes a tine 5100 that may, for example, be attached to an instrument such as instrument 4 shown in FIG. 2. The system 5000 also includes a tine acceptor 5200 that may, for example, be attached to an end tool. Alternatively, the tine 5100 may be located on the end tool and the tine acceptor 5200 may be located on an instrument.

Although FIGS. 28 and 29 show the tine 5100 as a stand-alone piece, it may be connected to or comprise other pieces, including additional tines and/or remote actuating systems. The tine 5100 may include a notch 5102 (also interchangeably referred herein as a retaining element). The tine may include any suitable number of notches 5102 for engaging an aspect of the tine acceptor 5200 or another portion of the system 5000.

The tine acceptor 5200 may include a clip 5202 (also interchangeably referred herein as a retainer extension), as shown in FIG. 28. The clip 5202 may be connected to the tine acceptor 5200 via a hinge 5204 that allows the clip 5202 to pivot with respect to the tine acceptor 5200. For example, the hinge 5204 may include a mechanism that biases the clip 5202, such that the clip 5202 normally engages a portion of the tine acceptor 5200, such as the clip acceptor portion

5206. The tine acceptor 5200 may further include a tine accommodating portion 5208.

Figure 30:
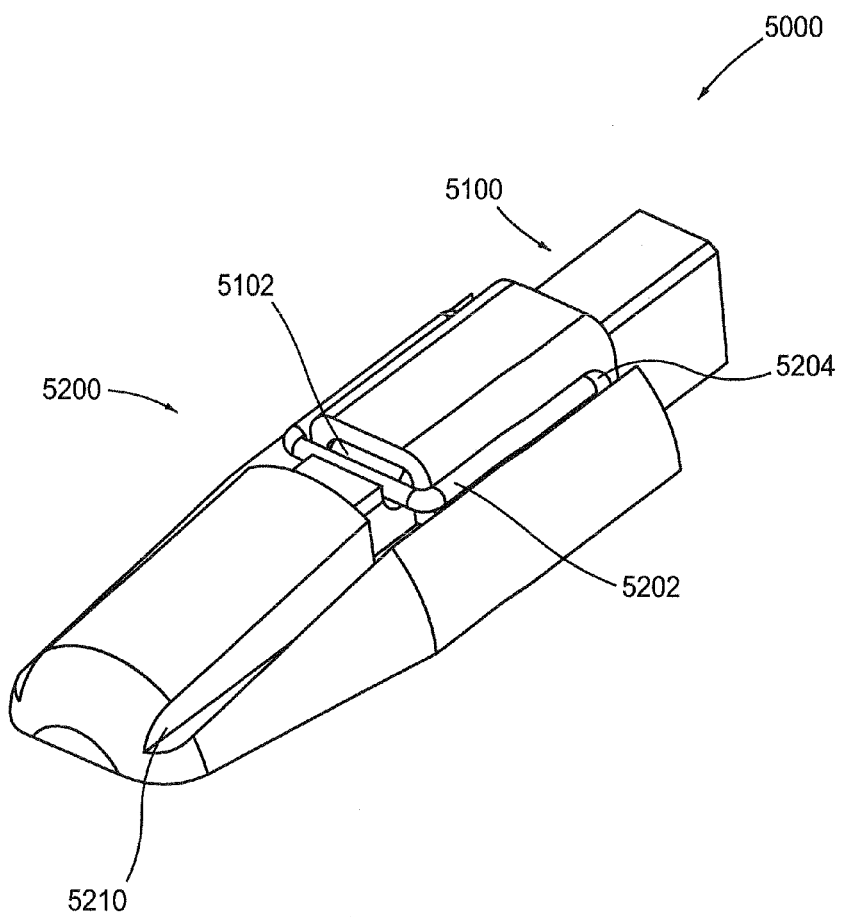
FIGS. 30-32 contain additional views of the system of FIG. 28, including detail on a clip engagement with a tine.
Figure 31:
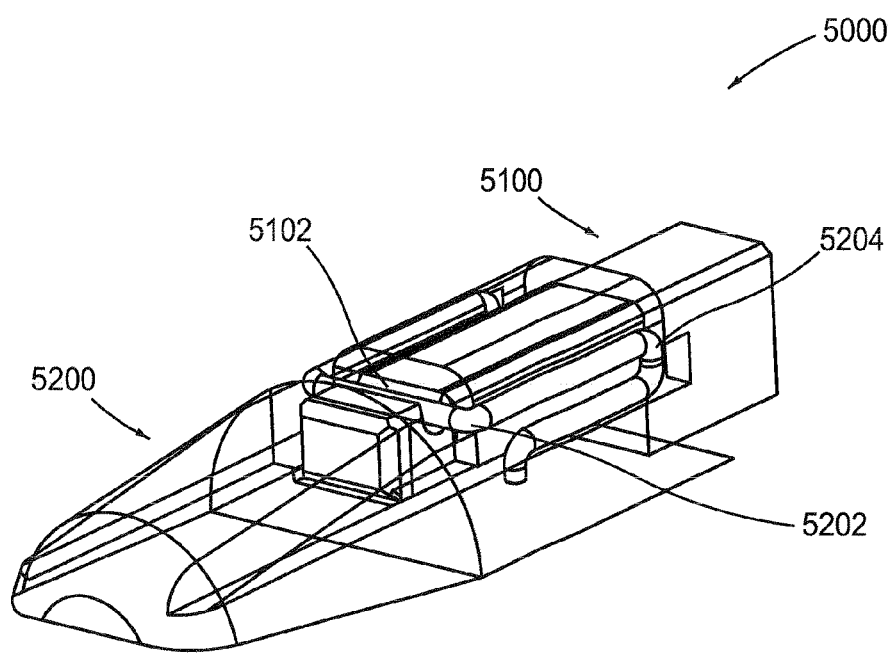
Figure 32:
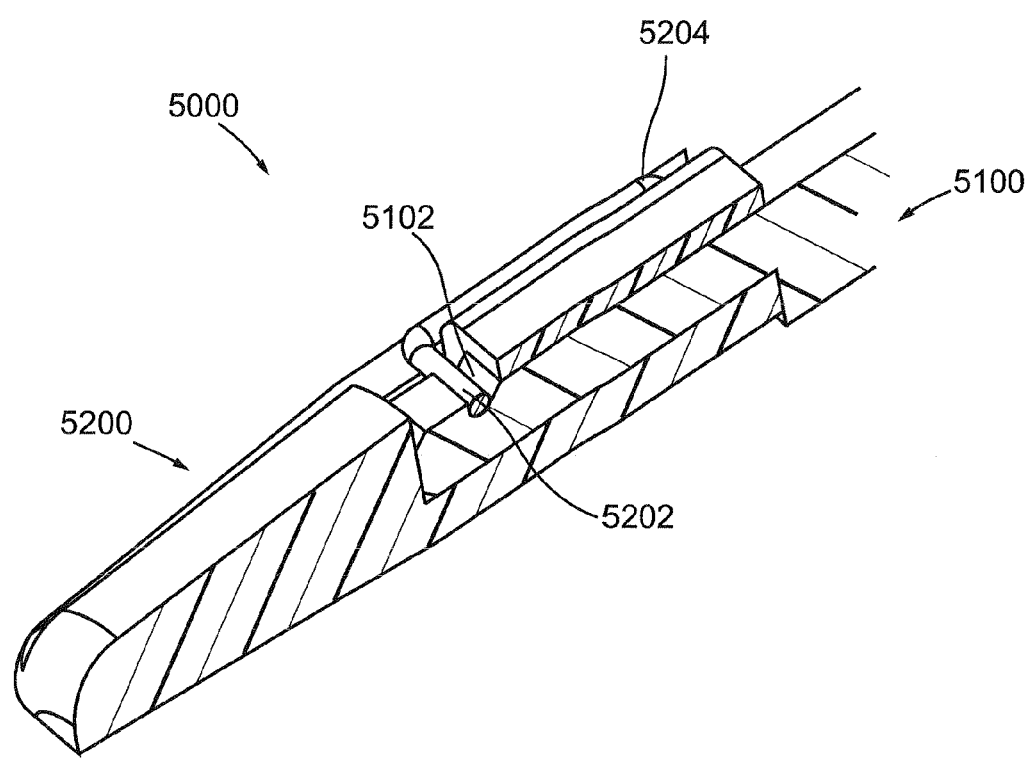

FIGS. 30-32 are views of the system of FIG. 28 with the clip shown engaged with the tine. FIG. 30 is a perspective view, FIG. 31 is a partially transparent perspective view, and FIG. 32 is a partial cutaway view. As shown in FIGS. 30-32, when the clip 5202 engages the tine 5100, the clip 5202 may rest in the notch 5102. This position may lock the tine 5100 in place inside the tine acceptor 5200. In particular, the bias imparted on the clip 5202 by the hinge 5204 may fix the clip 5202 in the notch 5102. Once thus fixed, the clip 5202 may be disengaged from the notch 5102 in a variety of ways. For example, an external lever tool may be engaged via channel 5210 (FIG. 30). The external lever tool may be used, for example, to disengage the clip 5202 by leverageably overcoming the bias imparted by the hinge 5204. Alternatively, any suitable mechanism for disengaging the clip 5202 may also be employed. For example, the clip may be disengaged by a lever applied via the tine 5100.

Although aspects the invention have been described with reference to various features and examples with respect to a surgical instrument, it is within the scope and spirit hereof to incorporate or use such features with any suitable mechanical device. Further, while aspects of the invention have been described with reference to a surgeon, another user may likewise perform various functions with such features, depending on circumstances in which used. Thus, it should be understood that numerous and various modifications may be made without departing from the spirit of hereof.

What is claimed is:

1. A system for exchanging at least one end tool comprising:
   at least one operating instrument engageable with each of the at least one end tool; and
   at least one tool exchange device, the at least one tool exchange device having:
     a tool retaining mechanism, the tool retaining mechanism having an opening for receiving the at least one tool; and
     a plurality of engagement features, the plurality of engagement features being configured to enable mutually exclusive engagement and disengagement of the tool retaining mechanism with each of the at least one tool,
   wherein each of the at least one tool has a biasing member engageable with the plurality of engagement features of the tool retaining mechanism, the biasing member being configured for biasing to an engaged position or biasing to a disengaged position.

2. The system for exchanging the at least one end tool of claim 1, wherein the plurality of engagement features comprises a ramp and a retaining element, and wherein the retaining element prevents axial movement of the at least one end tool.

3. The system for exchanging the at least one end tool of claim 2, wherein the retaining element includes a mating surface mateable with a portion of the biasing member.

4. The system for exchanging the at least one end tool of claim 2, wherein the biasing member is operably engageable with the ramp to disengage the operating instrument from the at least one end tool.

5. The system of exchanging the at least one end tool of claim 2, wherein the biasing member engages the ramp via a motion in a first direction along a longitudinal axis of the system.

6. The system of exchanging the at least one end tool of claim 2, wherein the biasing member is engagable with the retaining element while the biasing member maintains engagement with the ramp.

7. The system of exchanging the at least one end tool of claim 5, wherein the biasing member abuttably engages the retaining element during a motion in a second rotational direction of the at least one end toold about a longitudinal axis of the system.

8. The system of exchanging the at least one end tool of claim 2, wherein the engagement of ,the biasing member with the retaining element inhibits motion of the at least one end tool in a direction along a longitudinal axis of the tool exchange device.

9. The system for exchanging the at least one end tool of claim 1, wherein the plurality of engagement features comprises a release mechanism and a retention element.

10. The system for exchanging the at least one end tool of claim 9, wherein the retention element has a mating surface mateable with a portion of the at least one end tool.

11. The system for exchanging the at least one end tool of claim 9, wherein the biasing member is engageable with the release mechanism to disengage the operating instrument from the at least one end tool.

12. The system for exchanging the at least one end tool of claim 11, wherein the release mechanism comprises a projecting member that engages the biasing member to cause the biasing member to pivot about a pivot point.

13. The system of exchanging the at least one end tool of claim 9, wherein the biasing member is aligned with the release mechanism via a motion in a first direction along an axis transverse to a longitudinal axis of the system.

14. The system of exchanging the at least one end tool of claim 9, wherein the at least one end tool is engagable with the retention element contemporaneously with the release mechanism maintaining engagement with the biasing member.

15. The system of exchanging the at least one end tool of claim 13, wherein the at least one end tool is disengaged from the at least one instrument after engaging the release mechanism with the biasing member via a motion in a second direction along the longitudinal axis of the system.

16. The system of exchanging the at least one end tool of claim 9, wherein the release mechanism engages the biasing member via actuation of the release mechanism.

17. The system of exchanging the at least one end tool of claim 9, wherein the engagement of the at least one end tool with the retention element inhibits motion of the at least one end tool in a direction along a longitudinal axis of the tool exchange device.

18. A method for exchanging a plurality of tools comprising:
   providing an operating instrument engaged with an end tool, wherein the end tool has a biasing member;
   providing a tool exchange device having a plurality of engagement features;
   inserting the operating instrument engaged with an end tool into the tool exchange device along a first direction;
   engaging the biasing member with the plurality of engagement features; and
   with the biasing member maintaining engagement with the plurality of engagement features, moving the operating instrument and tool along a second direction contemporaneously, thereby releasing the operating instrument from the end tool.

19. The method for exchanging a plurality of tools of claim 18, wherein the first direction is along a longitudinal axis of the tool exchange device.

20. The method for exchanging a plurality of tools of claim 18, wherein engaging the biasing member with the plurality of engagement features further comprises moving the operating instrument in a rotational direction.

21. The method for exchanging a plurality of tools of claim 18, wherein the plurality of engagement features comprises a ramp and a retaining mechanism.

22. The method for exchanging a plurality of tools of claim 18, wherein the retaining mechanism comprises a mating surface mateable with a portion of the biasing member.

23. The method for exchanging a plurality of tools of claim 22, wherein engaging the biasing member with a retaining mechanism comprises abutting a portion of the biasing member with the retaining member, thereby inhibiting movement of the tool in direction along a longitudinal axis of the tool exchange device.

24. The method for exchanging a plurality of tools of claim 18, wherein the first motion is in a direction approximately opposite the second motion.

25. The method for exchanging a plurality of tools of claim 18, wherein the plurality of engagement features comprises a release mechanism and a retention element.

26. The method for exchanging a plurality of tools of claim 18, wherein the retention element comprises a mating surface mateable with a portion of the at least one end tool.

27. The method for exchanging a plurality of tools of claim 25, further comprising engaging the biasing member with the release mechanism to disengage the operating instrument from the at least one end tool.

28. The method for exchanging a plurality of tools of claim 27, wherein the release mechanism comprises a projecting member that engages the biasing member to cause the biasing member to pivot about a pivot point.

29. The method for exchanging a plurality of tools of claim 25, wherein inserting the operating instrument along the first direction aligns the biasing member with the release mechanism.

30. The method for exchanging a plurality of tools of claim 25, further comprising engaging the at least one end tool with the retention element contemporaneously with the release mechanism maintaining engagement with the biasing member.

31. The method for exchanging a plurality of tools of claim 25, wherein moving the operating instrument and the at least one end tool along the second direction disengages the at least one end tool from the operating instrument after engaging the release mechanism with the biasing member.

32. The method for exchanging a plurality of tools of claim 31, wherein engaging the release mechanism with the biasing member comprises actuating of the release mechanism.

33. The method for exchanging a plurality of tools of claim 25, wherein the engagement of the at least one end tool with the retention element inhibits motion of the at least one end tool in the second direction.

34. A system for exchanging at least one end tool comprising:
   at least one tool exchange device for retaining each of the at least one end tool, including:
   a tool retaining mechanism having an opening; and
   means for enabling mutually exclusive engagement and disengagement of the tool retaining mechanism with each of the at least one tool,
   wherein each of the at least one tool is receivable in the opening and has means for at least one of engaging or disengaging the means for enabling mutually exclusive engagement and disengagement; and
   at least one operating instrument engageable with each of the at least one end tool.

35. A retaining mechanism engageable with a tool exchange device, comprising:
   a tool exchange acceptor portion mateable with a portion of the tool exchange device; and
   a biasing member comprising a clip pivotable about a pivot point, the biasing member being operably engageable with a portion of an operating instrument,
   wherein the biasing member is configured to disengage from the portion of the operating instrument in response to the acceptor portion being engaged with the portion of the tool exchange device.

36. The retaining mechanism of claim 35, further comprising an operating instrument acceptor portion operably engageable with the portion of the operating instrument.

37. The retaining mechanism of claim 35, wherein the biasing member is configured to bias the clip to retainably engage a retaining element in the portion of the operating instrument.

38. The system for exchanging at least one end tool of claim 1, wherein the at least one tool exchange device is locatable within a patient body.

* * * * *